United States Patent
Garcia-Webb et al.

(10) Patent No.: US 7,485,100 B2
(45) Date of Patent: Feb. 3, 2009

(54) MICROSCOPIC DYNAMIC MECHANICAL ANALYZER

(75) Inventors: Michael Garcia-Webb, Cambridge, MA (US); Ian W. Hunter, Lincoln, MA (US); Andrew J. Taberner, Lexington, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 79 days.

(21) Appl. No.: 11/006,359

(22) Filed: Dec. 7, 2004

(65) Prior Publication Data

US 2006/0058607 A1 Mar. 16, 2006

Related U.S. Application Data

(60) Provisional application No. 60/606,327, filed on Aug. 31, 2004.

(51) Int. Cl.
*A61B 5/103* (2006.01)
*A61B 5/117* (2006.01)
*A61B 5/05* (2006.01)
*A61B 5/22* (2006.01)
*G01L 1/22* (2006.01)
*G01L 5/00* (2006.01)
*G01L 5/10* (2006.01)
*G01L 1/04* (2006.01)
*G01L 3/24* (2006.01)
*A63B 21/00* (2006.01)
*A63B 23/16* (2006.01)

(52) U.S. Cl. .................. 600/587; 600/595; 600/407; 73/862; 73/862.01; 73/862.41; 73/862.451; 73/379.01; 73/379.08

(58) Field of Classification Search ........... 600/585, 600/595, 407; 73/862, 862.01, 862.41, 862.42, 73/862.451, 379.01, 379.08
See application file for complete search history.

(56) References Cited

U.S. PATENT DOCUMENTS

| | | | | |
|---|---|---|---|---|
| 5,745,019 A | * | 4/1998 | Renger | 335/222 |
| 5,807,758 A | * | 9/1998 | Lee et al. | 436/526 |
| 5,961,540 A | * | 10/1999 | Renger | 607/32 |
| 2002/0178831 A1 | * | 12/2002 | Takada | 73/779 |
| 2003/0123124 A1 | * | 7/2003 | Abu-Ageel | 359/290 |
| 2003/0200820 A1 | * | 10/2003 | Takada et al. | 73/862.626 |

OTHER PUBLICATIONS

Bers, D.M., "Calcium Fluxes Involved in Control of Cardiac Myocyte Contraction," *Circ. Res.*, 87: 275-281 (2000).
Bers, D.M., "Cardiac Excitation-Contraction Coupling," *Nature*, 415: 198-205 (2002).
Brenan, C., et al., "Characterization and Use of a Novel Optical Position Sensor for Microposition Control of a Linear Motor," *Rev. Sci. Instrum.*, 64(2): 349-356 (Feb. 1993).

(Continued)

*Primary Examiner*—Max Hindenburg
*Assistant Examiner*—Jeffrey G Hoekstra
(74) *Attorney, Agent, or Firm*—Hamilton, Brook, Smith & Reynolds, P.C.

(57) ABSTRACT

An electromagnetic apparatus, comprises a conductive loop comprising two parallel conductive legs joined at a free end by a sample contacting member and a magnetic circuit that imposes a magnetic field in opposite directions across the respective legs. A method of mechanically characterizing a sample, comprises imposing a magnetic field in opposite directions in each of two parallel conductive legs of a conductive loop, the legs joined at a free end by a sample contacting member.

50 Claims, 12 Drawing Sheets

OTHER PUBLICATIONS

Campbell, K.B., et al., "Nonlinear Myofilament Regulatory Processes Affect Frequency-Dependent Muscle Fiber Striffness," *Biophys. J.*, 81: 2278-2296 (Oct. 2001).

Cheng, D.K., et al., "Nonuniform Responses of Transmembrane Potential During Electric Field Stimulation of Single Cardiac Cells," *Am. J. Physiol.*, 277(1 Pt. 2): H351-H362 (Jul. 1999).

Fabioto, A., "Computer Programs for Calculating Total from Specified Free or Free from Specified Total Ionic Concentrations in Aqueous Solutions Containing Multiple Metals and Ligands," *Methods Enzymol.*, 157: 378-416 (1988).

Garnier, D., "Attachment Procedures for Mechanical Manipulation of Isolated Cardiac Myocytes: A Challenge," *Cardiovascular Res.*, 28: 1958-1964 (1994).

Goldman, Y.E., "Measurement of Sarcomere Shortening in Skinned Fibers from Frog Muscle by White Light Diffraction," *Biophys. J.*, 52(1): 57-68 (Jul. 1987).

Kawai, M., et al., "Sinusoidal Analysis: A High Resolution Method for Correlating Biochemical Reactions with Physiological Processes in Activated Skeletal Muscles of Rabbit, Frog and Crayfish," *J. Muscle Res. Cell Motil.*, 1(3): 279-303 (Sep. 1980).

Kawai, M., et al., "Crossbridge Scheme and the Kinetic Constants of Elementary Steps Deduced from Chemically Skinned Papillary and Trabecular Muscles of the Ferret," *Circ. Res.*, 73(1): 35-50 (Jul. 1993).

Landesberg, A. et al., "Mechanical Regulation of Cardiac Muscle by Coupling Calcium Kinetics with Cross-Bridge Cycling: A Dynamic Model," *Am. J. Physiol.*, 267(2 Pt. 2): H779-H795 (Aug. 1994).

Noble, D., et al., "Models of Cardiac Ventricular Action Potentials: Iterative Interaction Between Experiment and Simulation," *Phil trans R Soc Lond A*, 359: 1127-1142 (2001).

Regnier, M., et al., "Regulation of the Cross-Bridge Transition from a Weakly to Strongly Bound State in Skinned Rabbit Muscle Fibers," *Am. J. Physiol.*, 269(6 Pt. 1): C1532-C1539 (Dec. 1995).

Swartz, D.R., et al., "Strong Binding of Myosin Increases Shortening Velocity of Rabbit Skinned Skeletal Muscle Fibres at Low Levels of $Ca^{2+}$," *J. Physiol.*, 533(Pt. 2): 357-365 (Jun. 1, 2001).

Stuyvers, B.D., et al., "Effect of Stimulation Rate, Sarcomere Length and $Ca^{2+}$ on Force Generation by Mouse Cardiac Muscle," *J. Physiol.*, 544(3): 817-830 (2002).

Stuyvers, B.D., et al., "Dynamics of Viscoelastic Properties of Rat Cardiac Sarcomeres During the Diastolic Interval: Involvement of $Ca^{2+}$," *J. Physiol.*, 502(3): 661-677 (1997).

van Heuningen, R., et al., "Sarcomere Length Control in Striated Muscle," *Am. J. Physiol.*, 242(3): H411-H420 (Mar. 1982).

Wang, G., et al., "Effect of Temperature on Elementary Steps of the Cross-Bridge Cycle in Rabbit Soleus Slow-Twitch Muscle Fibres," *J. Physiol.*, 531(1): 219-234 (Feb. 15, 2001).

Weiward, W.K., et al., "Sarcomere Length-Tension Relationship of Rat Cardiac Myocytes at Lengths Greater than Optimum," *J. Mol. Cell Cardiol.*, 32(2): 247-259 (Feb. 2000).

Deen, W.M., *Analysis of Transport Phenomena*. Oxford University Press, 1998.

Iwazumi, T., "High-Speed Ultrasensitive Instrumentation for Myofibril Mechanics Measurements," *Am. J. Physiol.*, 252(2 Part 1): C253-62 (Feb. 1987).

Luo, C.H. and Tung, L., "Null-Balance Transducer for Isometric Force Measurements and Length Control of Single Heart Cells," *IEEE Trans. Biomed.Eng.*, 38(12): 1165-1174 (Dec. 1991).

Lin, G., et al., "Miniature Heart Cell Force Transducer System Implemented in MEMS Technology," IEEE Trans. *Biomed. Eng.*, 48(9): 996-1006 (Sep. 2001).

Tasche, C., et al., "A Force Transducer for Measuring Mechanical Properties of Single Cardiac Myocytes," *Am. J. Physiol.*, 277(6 Pt 2): H2400-8 (Dec. 1999).

Stehle, R., et al., "Force Kinetics and Individual Sarcomere Dynamics in Cardiac Myofibrils After Rapid Ca2+ Changes," *Biophys. J.*, 83(4): 2152-61 (Oct. 2002).

\* cited by examiner

MICROSCOPIC DYNAMIC MECHANICAL ANALYZER

RELATED APPLICATION

This application claims the benefit of U.S. Provisional Application No. 60/606,327, filed on Aug. 31, 2004, the entire teachings of which are incorporated herein by reference.

GOVERNMENT SUPPORT

This invention was made with government support under Grant Number DAAD19-02-D-0002, awarded by the Army Research Office. The Government has certain rights in the invention.

BACKGROUND OF THE INVENTION

Mechanical characterization of biomechanical tissues, in particular muscle cells such as single cardiac myocytes is used to understand normal and disease states. In particular, it is desirable to characterize such tissues upon exposure to stimuli such as pharmaceuticals, electric fields, gene modification, and the like.

These difficult measurements are performed using a position actuator and a force transducer. A wide variety of systems have been explored in the art to explore the mechanics of cardiac myocytes (single cells), muscle tissue (groups of cells) or myofilaments (contractile apparatus within single cells), typically employing a combination of expensive precision commercial actuators and custom force sensors. These systems and their associated electronics, optics and fluidics are often bulky and not well suited to high throughput measurements.

One approach employs polysilicon beams in a fixed/cantilever arrangement with a piezoelectric strain gauge to measure displacement. Another approach employs a steel cantilever with an open loop piezoelectric transducer adapted from an atomic force microscope. Another group attached a myocyte to two compliant wire loops in a magnetic field and independently controlled the current in each.

SUMMARY OF THE INVENTION

There is a need in the art for a robust, high performance system, suitable for use in a high throughput studies that can mechanically characterize samples such as single cardiac myocytes.

An apparatus and method are provided for mechanically characterizing a sample.

An electromagnetic apparatus, comprises a conductive loop comprising two parallel conductive legs joined at a free end by a sample contacting member and a magnetic circuit that imposes a magnetic field in opposite directions across the respective legs.

A method of mechanically characterizing a sample, comprises imposing a magnetic field in opposite directions in each of two parallel conductive legs of a conductive loop, the legs joined at a free end by a sample contacting member.

Electric current can flow in opposite directions through the legs, which can result in movement of the member in a direction normal to its surface. The magnetic circuit can comprise a center magnetic pole aligned between two outer magnetic poles where the conductive loop can be electrically isolated from the poles, and the legs can be supported opposite each other across the center pole and between the outer poles. Typically, a magnetic field can be in the same plane as the major surface of the cantilever and is perpendicular to the major flexing direction of the cantilever.

A workpiece can oppose the sample contacting member to define a sample zone. The loop can be a conductive cantilever comprising the two legs at its supported end. A displacement sensor can be directed at the conductive cantilever. The workpiece can be the free end of a second conductive cantilever or can be an anvil.

A controller, which can be an automatic controller, can be electrically coupled to the legs of the cantilever, which can actuate the cantilever by applying current and can correlate the current with the force at the cantilever, e.g., between a loop defined by the cantilever and a sample. The controller can be coupled to the displacement sensor and can correlate force with displacement upon actuation of the cantilever. When the workpiece can be the free end of a second conductive cantilever, the controller can be electrically coupled to the legs of each cantilever, and the controller can independently actuate each cantilever by applying current and correlating the current with the force at each cantilever.

The displacement sensor can be directed at both conductive cantilevers and the controller can independently detect force as a function of displacement upon actuation of each cantilever. A second displacement sensor can be directed to the second conductive cantilever and coupled to the controller so that the controller can independently detect force as a function of displacement upon actuation of each cantilever.

The controller can comprise a feedback control loop that dynamically controls the displacement of a sample in the sample zone (e.g., to place the sample at the target of a sample analyzer). The controller can dynamically detect force and displacement of the cantilever over a bandwidth of at least about 250 Hz, typically from about 0 Hz to about 500 Hz, or more typically from about 0 Hz to about 1000 Hz. The controller can dynamically detect force of the cantilever at a resolution of about 100 nanoNewtons/$\sqrt{Hz}$, or more typically at a resolution of about 10 nanometers/$\sqrt{Hz}$.

The sample zone can be from about 1 micrometer to about 1000 micrometers across, and typically includes a biocompatible coating. The biocompatible coating can be selected from gold; titanium; titanium alloys; platinum; alloys of platinum, palladium, rhodium, iridium, ruthenium, and osmium; parylene; polymethyl methacrylate; polyethylene terephthalate; polypropylene; polytetrafluoroethylene; ultrahigh molecular weight polyethylene; polyethylene oxide; and polyvinyl pyrrolidone. A sample chamber can be included that encircles at least a portion of the conductive cantilever and the workpiece to support a liquid sample (e.g., a biocompatible liquid) in the sample zone. The sample chamber can optionally include: an inlet and an outlet (whereby the fluid can be flowed through the sample zone); a heat exchanger thermally coupled to the sample zone (whereby the temperature can be controlled); a plurality of electrodes, which can generate an electric field at the sample zone; a patch clamp sensor that can contact a sample in the sample zone; and/or an optical detector that can observe a sample in the sample zone.

The center pole can support a magnetic polarity opposite from the outer poles. The magnetic poles can support a magnetic field strength between the center pole and each outer pole from about 0.1 Tesla to about 2.5 Tesla. The magnetic poles can be: a permanent magnetic material selected from alinco magnets, hard ferrite magnets, samarium cobalt magnets, and neodymium iron boron magnets; a magnetic permeable material selected from amorphous alloys; nano-crystalline alloys; soft ferrites; MnZn ferrite; microwave ferrites; and vanadium Permandur. The poles can be coupled to an electromagnet or a permanent magnetic material selected from alinco magnets, hard ferrite magnets, samarium cobalt magnets, and neodymium iron boron magnets.

Each conductive cantilever can have a stiffness (at 0 Hz) from about 0.1 to about 50 Newtons/meter, and can have a first resonant frequency in air of between about 100 Hz to about 50,000 Hz. The conductive cantilever can be made from a material selected from a metal and a doped semiconductor, for example: a metal selected from gold, platinum, copper, titanium, aluminum, steel alloys; nickel alloys; copper alloys; aluminum alloys; cobalt-chromium alloys; titanium alloys; and stainless steel 304; or a doped semiconductor selected from doped silicon; silicon dioxide; silicon nitrite, CdTe, CdSe, CdS, ZnS, GaAs, GaN, AlGaN, InGaN, GaP, InP, InAsP, Si, Ge, ZnO, $SnO_2$, $TiO_2$, $Cr_{2-x}Ti_xO_3$, $WO_3$, SiC, $Fe_2O_3$, $In_2O_3$, $Ga_2O_3$, $SrTiO_3$, $BaTiO_3$, $CaTiO_3$, $(La,Sr)FeO_3$, $(La,Sr)CoO_3$, and indium tin oxide.

A sample can be characterized by the apparatus and method for dynamic stiffness; creep recovery; a rate of tension redevelopment (e.g., in a muscle cell); force (e.g., force produced by a muscle cell compared to Ca2+ concentration; a time constant of relaxation (e.g., time constant of relaxation of a muscle cell); and the like.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

In FIG. 1A poles 110 and 112 are of opposite polarity. In FIG. 1B poles 110 and 112 are the same polarity and oppose each other to define a gap. In FIG. 1C, a third pole 114 is included, which is aligned between poles 110 and 112.

DETAILED DESCRIPTION OF THE INVENTION

A description of preferred embodiments of the invention follows.

The methods and apparatus herein make use of the Lorentz force, where a force is created in a conductor in a magnetic field when current is passed through the conductor according to the following relation:

$$\vec{F} = L \cdot \vec{I} \times \vec{B} \quad (1)$$

where F is force, I is current, B is the magnetic field and L is the length of the conductor in the magnetic field. Thus, force is maximized when current is in a direction perpendicular to the field and minimized when the current is parallel to the field.

Figure 1A:
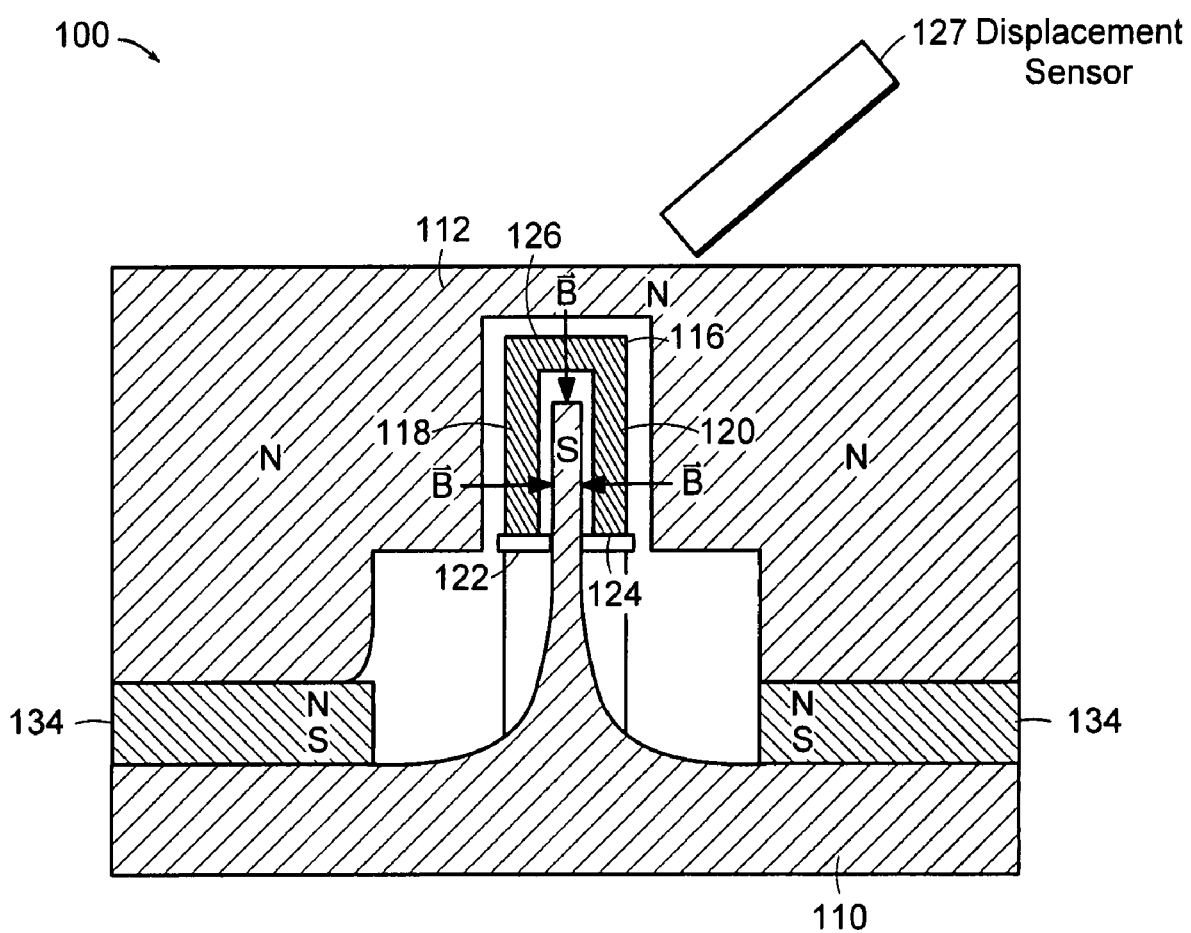
FIGS. 1A-1C depict various embodiments of an electromagnetic apparatus 100.
Figure 1B:
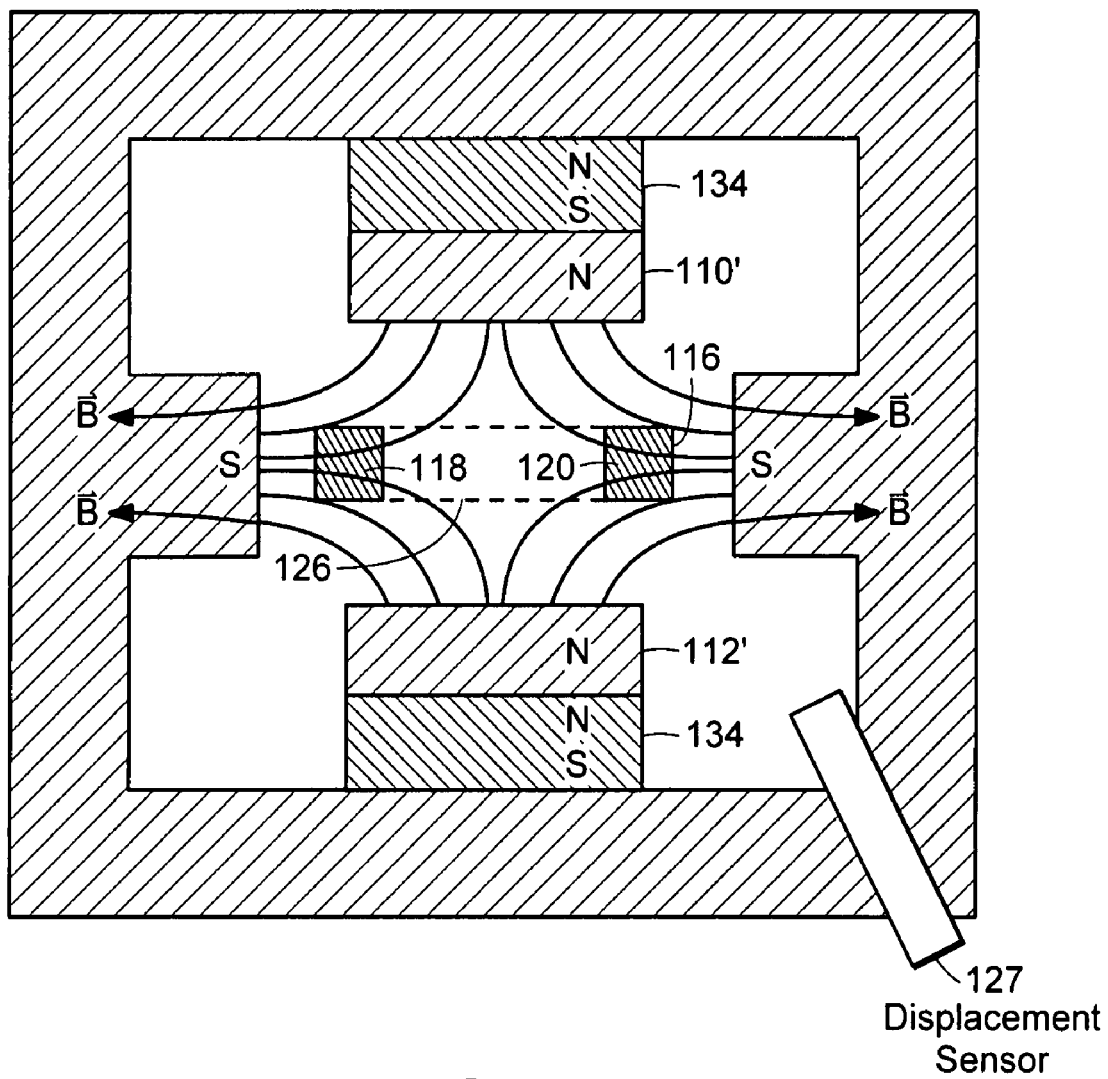
Figure 1C:
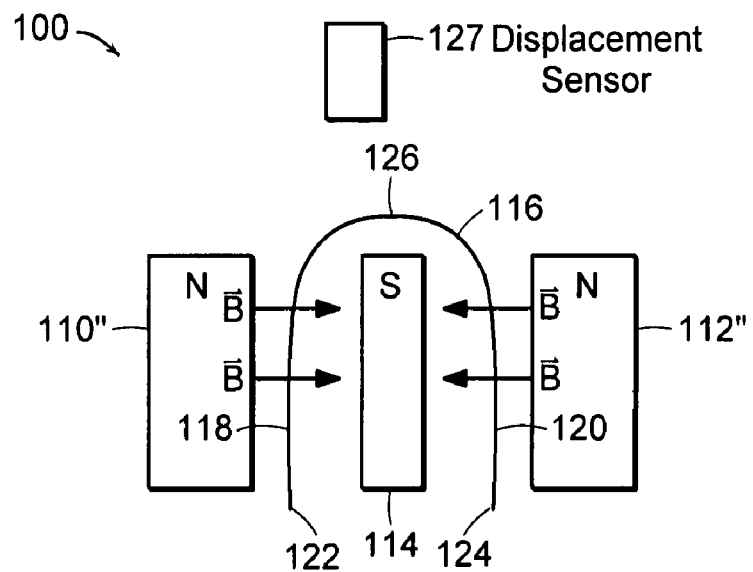

FIGS. 1A-1C depict various embodiments of an electromagnetic apparatus 100. Apparatus 100 includes first and second magnetic poles 110 and 112. Conductive loop 116 has two legs 118 and 120 and is electrically isolated (e.g., separated by one or more insulators such as air, insulating fluids, glass, polymers, polymeric coatings, and the like) from poles 110 and 112. Legs 118 and 120 are mechanically supported between poles 110 and 112 at regions 122 and 124 and thus region 126 of loop 116 can be considered its unsupported end. An optional displacement sensor 127 can be directed at loop 116, e.g., at unsupported end region 126 where typically the range of motion of loop 116 is the greatest. The magnetic poles direct a magnetic field in opposite directions in each leg as indicated by the arrows, e.g. generated by magnets 134. The relative polarity of poles (North or South) and direction of fields B can be as depicted in the FIGs or can be reversed. The sign or direction of the current through loop 116 can determine the direction of force or movement relative to the magnetic field.

In FIG. 1A poles 110 and 112 are of opposite polarity, legs 118 and 120 are supported across pole 110, and legs 118 and 120 and pole 110 extend into a cavity defined by pole 112. The field is in opposite directions in legs 118 and 120, and is perpendicular to the current flow in much of loop 116, including legs 118 and 120 and sample contacting member 126. Thus, application of current to apparatus 100 as depicted in FIG. 1A can cause motion of loop 116 in and out of the plane of the page depending on the direction of the current flow and the relative polarity of poles 110 and 112. The sample contacting member 126 can thus act upon or be acted upon by a sample, e.g., a cell positioned at or adjacent to sample contacting member 126.

In FIG. 1B poles 110' and 112' are the same polarity and oppose each other to define a gap. Conductive loop 116 is depicted in an end-on view where legs 118 and 120 are shaded. The opposition of poles of the same polarity creates a bidirectional field that flows in opposite directions in each leg. Thus, application of current to apparatus 100 as depicted in FIG. 1B can cause motion of loop 116 back and forth between poles 110' and 112', depending on the direction of the current flow and the relative polarity of poles 110' and 112', as above typically with greater deflection at unsupported end region 126. The magnetic field can be generated, by, e.g. magnets 134.

In FIG. 1C, a third pole 114 is included, which is aligned between poles 110 and 112. Poles 110" and 112" are both at a polarity opposite from the polarity of pole 114. In such three pole embodiments, legs 118 and 120 are supported across third pole 114, or in other words, pole 114 extends into a gap defined by loop 116. Thus, the magnetic field direction travels through the spaces between third pole 114 and poles 110" and 112", and the field is in opposite directions in legs 118 and 120.

Conducting loop 116 can be in the form of a wire or any other shape that forms an open loop. Typically, conducting loop 116 is a conducting cantilever, in other words a beam that has a supported end and a free end.

Conducting loop 116 can be an open loop of any conducting material, e.g., a metal, a doped semiconductor, and the like.

Examples of suitable metals can include pure metals such as gold, platinum, copper, titanium, aluminum, and the like; alloys, e.g., steel alloys (such as combinations of iron, chromium, nickel and carbon); nickel alloys (such as combinations of nickel, molybdenum, copper and iron); copper alloys (such as combinations of copper, zinc, tin, phosphor and beryllium) aluminum alloys; cobalt-chromium alloys; titanium and Ti-6Al-4V alloys; and the like. In some embodiments, loop 116 is constructed of stainless steel 304, an alloy of iron, chromium and nickel.

Examples of doped semiconductors include doped silicon; silicon dioxide; silicon nitrite, CdTe, CdSe, CdS, ZnS, GaAs, GaN, AlGaN, InGaN, GaP, InP, InAsP, Si, Ge, ZnO, $SnO_2$, $TiO_2$, $Cr_{2-x}Ti_xO_3$, $WO_3$, SiC, $Fe_2O_3$, $In_2O_3$, $Ga_2O_3$, $SrTiO_3$, $BaTiO_3$, $CaTiO_3$, $(La,Sr)FeO_3$, $(La,Sr)CoO_3$, indium tin oxide, and the like. The conductivity or mechanical properties can be improved using a coating such as Al, Au, Ti, W, Cu. Cr, Pd, Pt, Ir or Zn or alloys such as Ni—Fe and Al—Si—Cu, and the like.

Figure 2A:
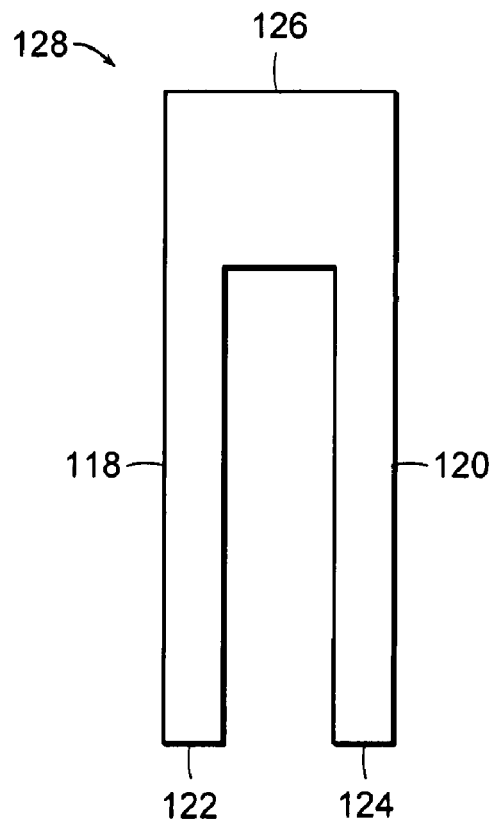
FIG. 2A shows an embodiment of the conducting loop as conducting cantilever 128, where legs 118 and 120 define a cutout allowing cantilever 128 to function as an open loop through which the current can be directed.

FIG. 2A shows an embodiment of the conducting loop as conducting cantilever 128, where legs 118 and 120 define a cutout allowing cantilever 128 to function as an open loop through which the current can be directed. Cantilever 128 has a supported end at regions 122 and 124 at the base of legs 118 and 120, and a free end at region 126. Typically, cantilever 128 can have a shape which has a major face (e.g., the face depicted in the plane of the page in FIG. 2A). When such a cantilever is employed in the apparatus configurations shown in FIGS. 1A-1C (substituted for conducting loop 116), for example, a surface of the cantilever can be normal to the motion direction of the cantilever.

Figure 2B:
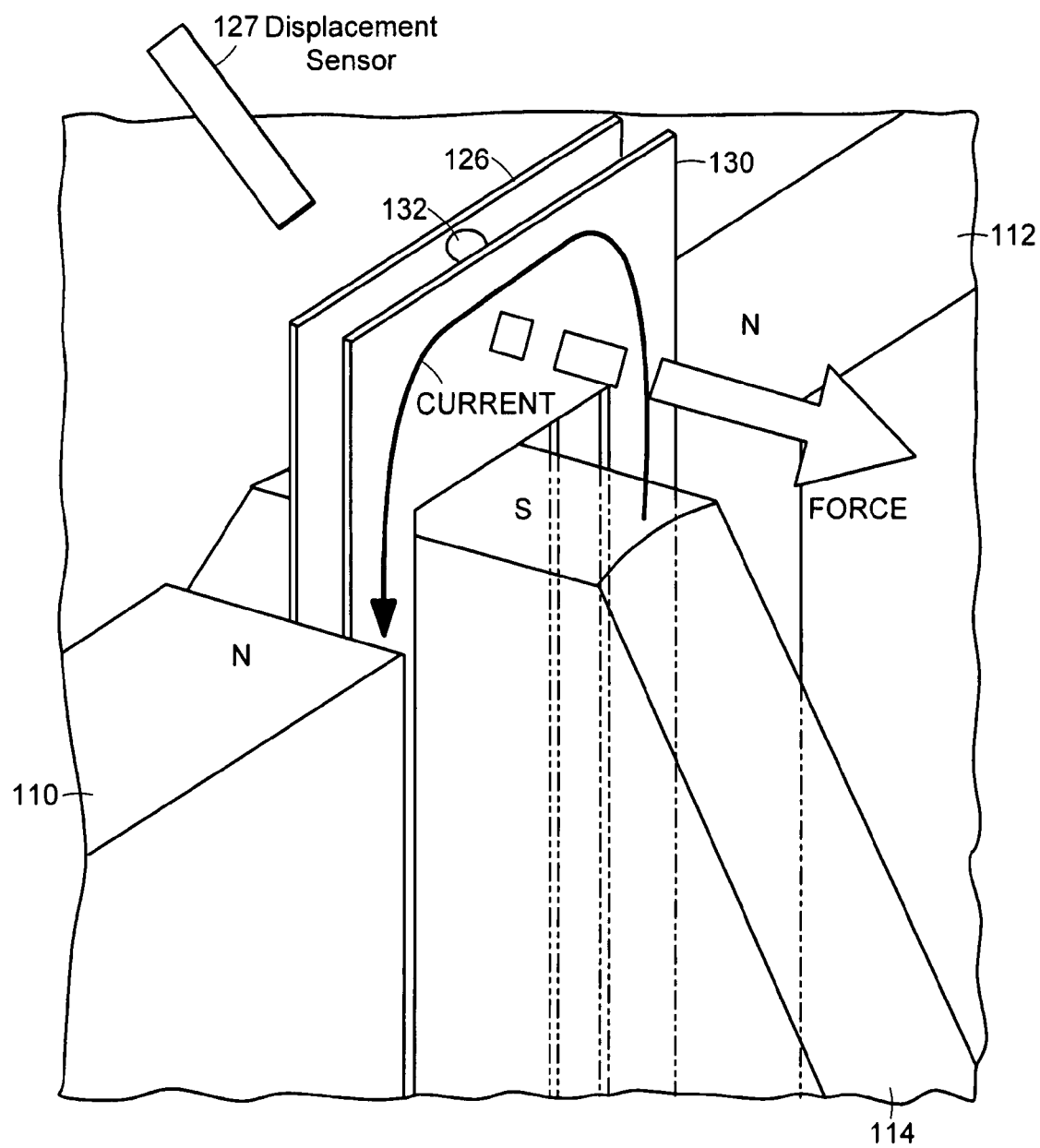
FIG. 2B depicts a side view wherein cantilever 128 opposes a workpiece 130 to define a sample zone. A sample 132 can be placed between the faces of cantilever 128 and workpiece 130.

FIG. 2B depicts a side view wherein cantilever 128 opposes a workpiece 130 to define a sample zone. The workpiece can be an anvil, in other words a static face against which cantilever 128 can exert a force. An anvil can be any solid substrate, an electrode, a window or lens to an optical detector, a conventional transducer or force sensor (e.g., a piezoelectric transducer) and the like. Typically, workpiece 130 is also a conductive cantilever.

Figure 2C:
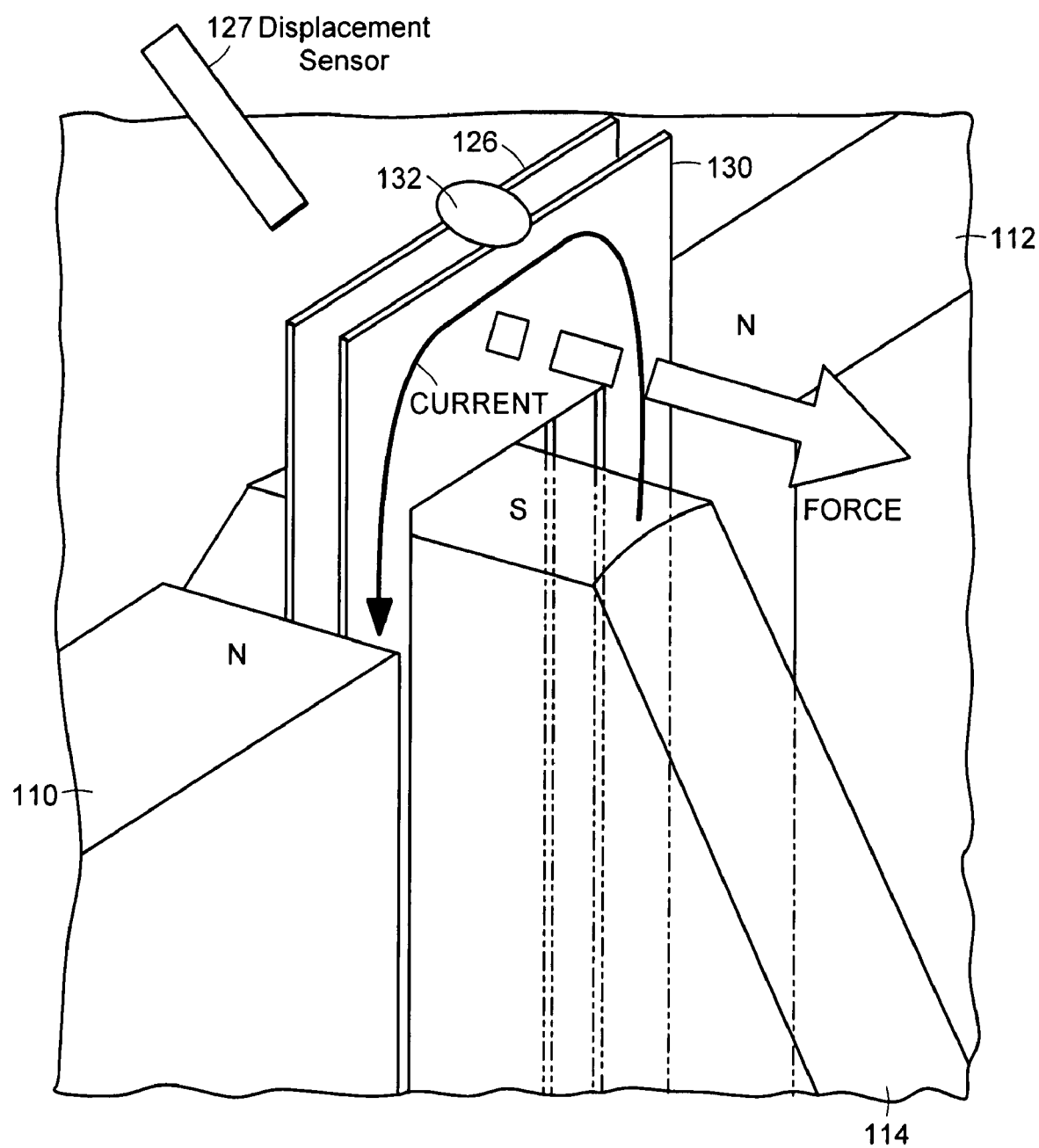
FIG. 2C depicts sample 132 placed to contact the edges of cantilever 128 and workpiece 130.

The sample zone includes the area between and around cantilever 128 and workpiece 130. For example, a sample 132 can be placed between the faces of cantilever 128 and workpiece 130 as depicted in FIG. 2B. A sample 132 can also be placed to contact the edges of cantilever 128 and workpiece 130 as depicted in FIG. 2C. Generally, the size of the sample zone, e.g., the distance between the faces of cantilever 128 and workpiece 130, is from about 1 micrometer to about 1000 micrometers across, typically from about 10 micrometers to about 500 micrometers across, and more typically from about 50 micrometers to about 150 micrometers across.

Samples can include any material for which mechanical characterization is desired. Typical samples include biological tissues, for example, structural tissues such as bone, cartilage, tendon, and the like, and muscle tissues, e.g., smooth muscle, skeletal muscle, and cardiac muscle. In some embodiment, the sample is a single cardiac myocyte. For example, myocytes can be isolated from animal models (Guinea pig, rat or mouse) using common enzymatic techniques; see O'Connell T, Ni Y. "Isolation of adult mouse cardiac myocytes from one heart." AFCS Procedure Protocol PP00000125 Version 1. URL http://www.signaling-gateway.org/data/cgi-bin/ProtocolFile.cgi/afcs_PP00000125.pdf?pid=PP00000125, November 2002; the entire contents of which are incorporated herein by reference. Other samples which can be examined include, for example, engineered materials such as artificial polymer muscle, materials synthesized by conventional and combinatorial methods, and the like.

Samples can be attached by any means known to the art, for example, by employing adhesives, electrostatic attachment, chemical bonding, and the like. A typical means of attachment, for example for biological tissues is to employ carbon fiber as discussed in Garnier D. "Attachment procedures for mechanical manipulation of isolated cardiac myocytes: a challenge". Cardiovascular Res. 1994; 28: 1958-1964, the entire teachings of which are incorporated herein by reference.

In various embodiments, the sample zone can include a biocompatible coating at the sample zone. Biocompatible coatings (including metallic and polymer coatings) are materials that can limit or prevent interaction of cells or molecules in solution with the boundaries of the sample zone and the cantilevers. Examples of the interactions that can be limited include adhesion, adsorption or desorption and electrochemical reactions (including oxidation or reduction reactions at the surfaces). Examples of suitable biocompatible metallic coatings include gold, titanium or its alloys including Ti-6Al-4V and platinum or alloys of the platinum metal group including platinum, palladium, rhodium, iridium, ruthenium, osmium, and the like. Examples of suitable biocompatible polymer coatings include are parylene, polymethyl methacrylate, polyethylene terephthalate, polypropylene, polytetrafluoroethylene, ultrahigh molecular weight polyethylene, polyethylene oxide, polyvinyl pyrrolidone, and the like. Further details of biocompatible coatings are known to the art; see, for example, Dee K C, Puleo D A and Bizios R. "An introduction to tissue-biomaterial interactions." John Wiley & Sons. 2002, the entire teachings of which are incorporated herein by reference.

Typically, a conductive cantilever is selected for particular mechanical properties suitable to the properties of the samples being characterized. For example, for measuring biological tissues such as muscle cells, the cantilever is generally constructed to have a stiffness at 0 Hz of between about 0.1 Newtons/meter to about 50 Newtons/meter, typically between about 1 to about 15 Newtons/meter. The cantilever can have a first resonant frequency in air from about 100 Hz to about 50,000 Hz, typically between about 250 Hz to 10,000 Hz, and more typically between about 500 Hz to about 1500 Hz.

As used herein, magnetic poles, e.g. poles 110, 112, and 114, can be any material that directs, guides, transmits, focuses, and/or generates a magnetic field.

For example, magnetic poles can be made of a permanent magnetic material. Examples of suitable permanent magnetic materials include alinco magnets (both cast and sintered), hard ferrite (or ceramic) magnets, samarium cobalt magnets, neodymium iron boron magnets, and the like.

Magnetic poles can be made of a magnetic permeable material that is not itself a permanent magnet, or that can be considered a soft magnetic material. Examples of suitable magnetic permeable materials for the poles include amorphous & nano-crystalline alloys (typically alloys including iron, nickel and/or cobalt with one or more of the following elements: boron, carbon, phosphorous and silicon; typically iron-silicon alloys or nickel-iron alloys); soft ferrites (e.g., ferrimagnetic materials with a cubic crystal structure and the general composition $MO.Fe_2O_3$, where M is a transition metal such as nickel, manganese or zinc); MnZn ferrite (also known as ferroxcube); microwave ferrites (e.g. as used in the frequency range from 100 MHz to 500 GHz, for waveguides for electromagnetic radiation and in microwave devices such as phase shifters, for example materials like yttrium iron garnet).

In various typical embodiments, the poles can channel a 0 Hz magnetic field from a permanent magnet to the gap between the poles, so peak flux density (saturation flux density) can be, in some embodiments, more important than magnetic permeability or the amount of energy that can dissipate in the material as the magnetic flux within it changes. Thus, in some embodiments, a preferred magnetic permeable material is Vanadium Permandur as it typically saturates at a very high magnetic flux density.

In various embodiments, the magnetic poles, typically when made of a magnetic permeable material, can be coupled to another magnetic source such as a permanent magnet or an electromagnet (e.g., a conventional or superconducting electromagnet). The magnetic poles generally support a magnetic field strength between adjacent poles (in the region occupied by the legs of conductive loop 116) of between about 0.1 Tesla and about 2.5 Tesla, typically between about 0.5 Tesla and about 2 Tesla, and more typically between about 0.7 Tesla and about 1.5 Tesla.

Figure 3A:
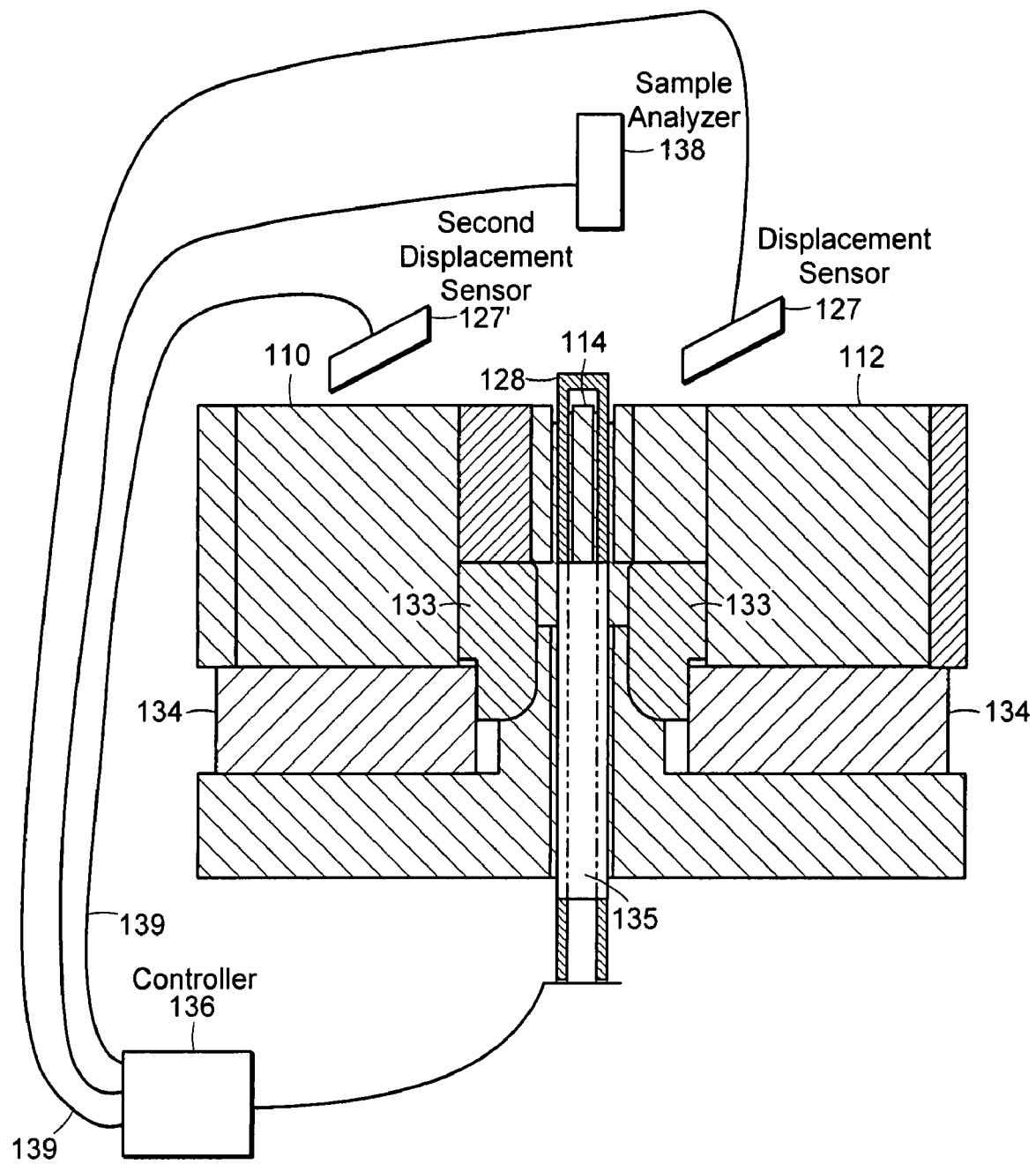
FIG. 3A depicts a two-dimensional view of a preferred embodiment of apparatus 100 wherein poles 110, 112, and 114 are made of Vanadium Permandur, and are coupled to a permanent magnet 134.
Figure 3B:
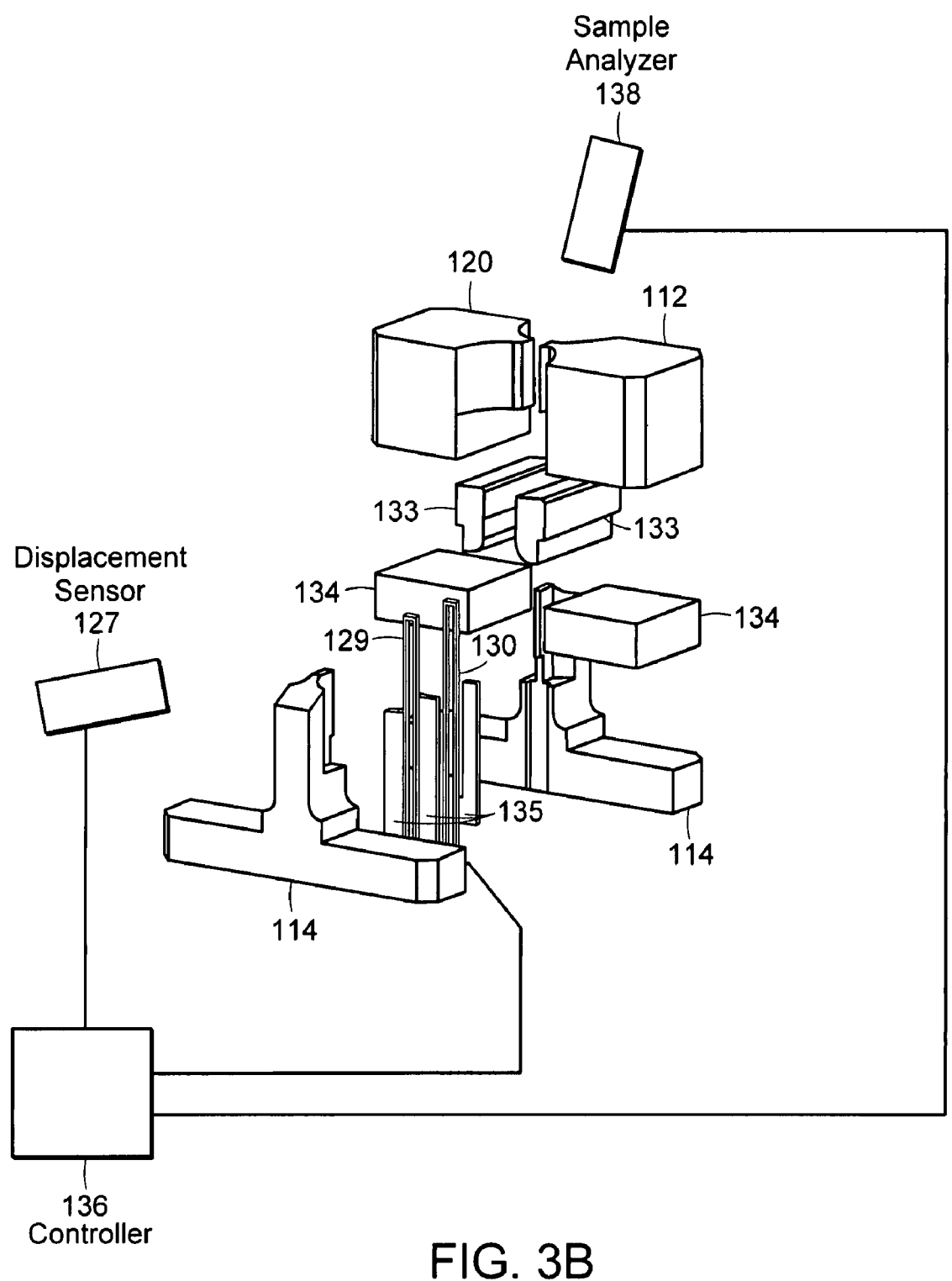
FIG. 3B depicts an isometric exploded view of the pieces in FIG. 3A.

For example, FIG. 3A depicts a two-dimensional view of a preferred embodiment of apparatus 100 wherein poles 110, 112, and 114 are made of Vanadium Permandur, and are coupled to permanent magnets 134 (e.g., made of neodymium iron boron). FIG. 3B depicts an isometric exploded view of the pieces in FIG. 3A. Note that in the exploded view of FIG. 3B, workpiece 130 is depicted as a second conductive cantilever; in the view in FIG. 3A, workpiece 130 is hidden by cantilever 128. Also depicted are aluminum blocks 133 (used hold the top keeper away from the center keeper and maintain the air gap) and glass insulating cover slides 135.

FIGS. 3A and 3B also show embodiments of apparatus 100 including a controller 136. Controller 136 is electrically coupled to the legs of the cantilever, and can actuate each cantilever by applying current. Controller 136 can correlate the current with the force at the cantilever, either by calculation using the Lorentz force relation above (Eq. (1)) or through a calibration table constructed by measuring the current versus force at cantilever 128 measured using a calibration sensor. When workpiece 130 is also a conductive cantilever, Controller 136 can be electrically coupled to the legs of each cantilever, and the controller can independently actuate each cantilever.

The force applied to the tip of each cantilever can be calculated by measuring the displacement of the tip of the cantilever (via displacement sensor 127) and using the known relationship between displacement at that point and applied force. This relationship is the dynamic stiffness of the cantilever which can be found using a mechanical test described below. The force measured by displacement is the sum of force applied by the sample (e.g., from the dynamic behavior of a contracting/relaxing muscle cell) and force applied by passing current through the cantilever.

Typically, the minimum resolvable force that can be detected by measuring tip displacement is limited by the resolution of displacement sensor 127. In some embodiments, the displacement sensor can be capable of detecting a peak displacement of 500 μm and can have a minimum resolvable displacement of 10 nanoNewton root mean squared (10 $nN_{RMS}$) over the measurement bandwidth.

To measure the minimum resolvable position, the displacement sensor can be pointed at a stationary cantilever and the power spectra of the resulting displacement signal estimated and expressed in units of meters$^2$/Hz (wherein the initial displacement signal is appropriately scaled to convert it to an effective displacement). The minimum resolvable displacement over the measurement bandwidth can be defined as the square root of the integral of the power spectra over the measurement bandwidth (for example, from 0 Hz to 1000 Hz). This value can be equivalent to the variance of the position signal after it had been passed through an ideal filter that allowed frequencies within the measurement bandwidth to pass unaltered and that blocked signal content at all other frequencies (for example an ideal low pass filter with a cut off at 1000 Hz).

In some embodiments, the peak force that can be applied by passing current through the cantilever is 500 μN. The minimum resolvable force (due to current) can be related to the ability to detect the current applied and typically can be less than 10 $nN_{RMS}$ over the measurement bandwidth. To measure this a constant current can be applied and the power spectra of the current monitoring signal can be estimated and expressed in units of Newtons$^2$/Hz (after an appropriate conversion from the actual unit of the current monitoring circuit). The minimum resolvable force can be defined as the square root of the integral of the power spectra over the measurement bandwidth.

Controller 136 can also be electrically coupled to displacement sensor 127, and can correlate the force with displacement upon actuation of cantilever 128. A single displacement sensor 127 can be employed to detect the position of either or both of cantilever 128 and workpiece/cantilever 130. Preferably, when workpiece 130 is also a cantilever, two displacement sensors 127 and 127' are employed to independently detect the position of each cantilever. Examples of suitable displacement sensors can include, for example, optical sensors such as interferometers, confocal systems, displacement of a laser beam reflected from the device, hall effect sensors, capacitive sensors, strain gauges, and the like.

Additional sensors, e.g., sample analyzer 138 can be directed at sample 132. Other sample sensors that can be used include, for example: optical sensors operating using ultraviolet light, visible light, infrared light, fluorescence, and the like, such as optical spectrometers, microscopy (e.g., including confocal microscopy), digital cameras, scanners, video cameras, and the like; electrodes, e.g., for electrochemical or electrophysiological measurements such as electrophysiology measurements conducted using a patch clamp apparatus; and the like.

For example, it can be important to consider sarcomere length when making physiological measurements of muscle due to its influence on force and dynamics and to ensure uniform sarcomere length is maintained if inferences are to be made between contraction of whole muscle cells and the kinetics of steps in the cross bridge cycle. Optical measurements of sarcomere length can be performed by either diffraction or direct imaging methods.

The diffraction of light caused by the rough crystalline structure of the A-I band has been observed since the nineteenth century. It was first applied to cardiac papillary muscle in using a laser beam and a video camera and suffered from broad diffraction lines due to structural heterogeneity of multiple cellular preparations. Single cells provide much clearer diffraction patterns and multiple theoretical and experimental approaches have been used to explore interpretations of the separation, intensity, fine structure and dynamics of these patterns. Thus, employing laser diffraction in sample analyzer 138 can give spacing of the diffraction pattern and thus a measure of average sarcomere length with sarcomeres modeled as a plane grating. This relationship is typically approximate and does not account for structural heterogeneity, Brag effects due to crystalline structure of the myocyte and spatially asynchronous behavior. Laser diffraction is still being used as a measure of sarcomere length as it simple to implement and has high bandwidth (2 to 28 kHz) so can be used online for control.

Performing direct imaging of sarcomeres at sample analyzer 138 with bright field, interference or polarizing microscopes using high quality, high numerical aperture optics and high bit rate CCD cameras can provide considerably more information than laser diffraction at the cost of complexity, physical size and money. Frame rates of 200 to 250 Hz have been achieved in the art, and off line processing, typically using spatial Fourier transforms, can be employed to find sarcomeric periodicity. This technique can be useful in myofibril preparations where A-I band overlap contrast can be high enough to monitor the length of individual sarcomeres.

Generally, the controller 136 dynamically detects force and displacement of the cantilever over a bandwidth of at least about 250 Hz; typically, the controller dynamically detects force and displacement of the cantilever from about 0 Hz to about 500 Hz; or more typically, the controller dynamically detects force and displacement of the cantilever from about 0 Hz to about 1000 Hz. In various embodiments, the controller can dynamically detect force of the cantilever at a resolution of about 100 nanoNewtons/$\sqrt{Hz}$, more typically about 50 nanoNewtons/$\sqrt{Hz}$, more typically about 10 nanoNewtons/$\sqrt{Hz}$, or preferably about 1 nanoNewtons/$\sqrt{Hz}$. In some embodiments, the controller dynamically detects displacement of the cantilever at a resolution of about 10 nanometers/$\sqrt{Hz}$, more typically about 5 nanometers/$\sqrt{Hz}$, more typically about 1 nanometer/$\sqrt{Hz}$, or preferably more typically about 0.1 nanometer/$\sqrt{Hz}$.

The controller and its associated programming can include typical analog circuits and/or digital circuits known to the art or adaptable from the art, commercial data acquisition systems (National Instruments, Austin Tex.) neural networks, and the like.

A desired force or position signal can be applied to a sample by applying an appropriate current to the arms of the cantilever creating a force which in turn results in a displacement of the tip of the cantilever and can change the length of the sample. This displacement can be detected by displacement sensor 127 which typically produces an analog voltage proportional to displacement, which can then be converted to a digital signal using a data acquisition system. The current (and thus force) applied can also be captured by the data acquisition system, and the digital force and position data can provide the input to a control algorithm (e.g., a proportional integral derivative (PID) loop, a statespace controller designed using optimal control, and the like) which can adjust the input so that a desired length change can be applied to the sample (position control) or so that a desired force can be applied to the sample (force control). The force and position data from each cantilever can be processed simultaneously to extract information about the mechanical properties of the system.

The position and force feedback control algorithms and desired experimental protocols can be written in (for example) C, C++, VB, Java and the like and then compiled into appropriate assembly language for a digital signal processor (DSP). They can also be written directly in the assembly language or in a combination of the two. An integrated digital data acquisition and control circuit can include, for example, analog to digital converters (ADCs) and digital to analog converters (DACs) which can convert the analog signals from sensors to digital signals and convert the digital control signals to analog outputs; on board memory which can be used to store experimental protocols or data; a module which can stream experimental data or download code to a computer, for example, an Ethernet, universal serial bus (USB), Firewire or Bluetooth module or the like; and CPLD (complex programmable logic device) or (field programmable gate array) programmed in VHDL (Very High Speed Integrated Circuit (VHSIC) Hardware Description Language) which can coordinate the elements of such digital systems.

When workpiece 130 is also a cantilever, the controller can include a feedback control loop 139 that dynamically controls the displacement of a sample 132 in the sample zone. For example, when sample 132 is a muscle cell, the cell can expand or contract, and the feedback control loop 139 can be operated to control the cantilevers to keep the muscle cell at a particular location, e.g., centered with respect to a sample sensor such as sample analyzer 138 directed at sample 132.

Figure 4:
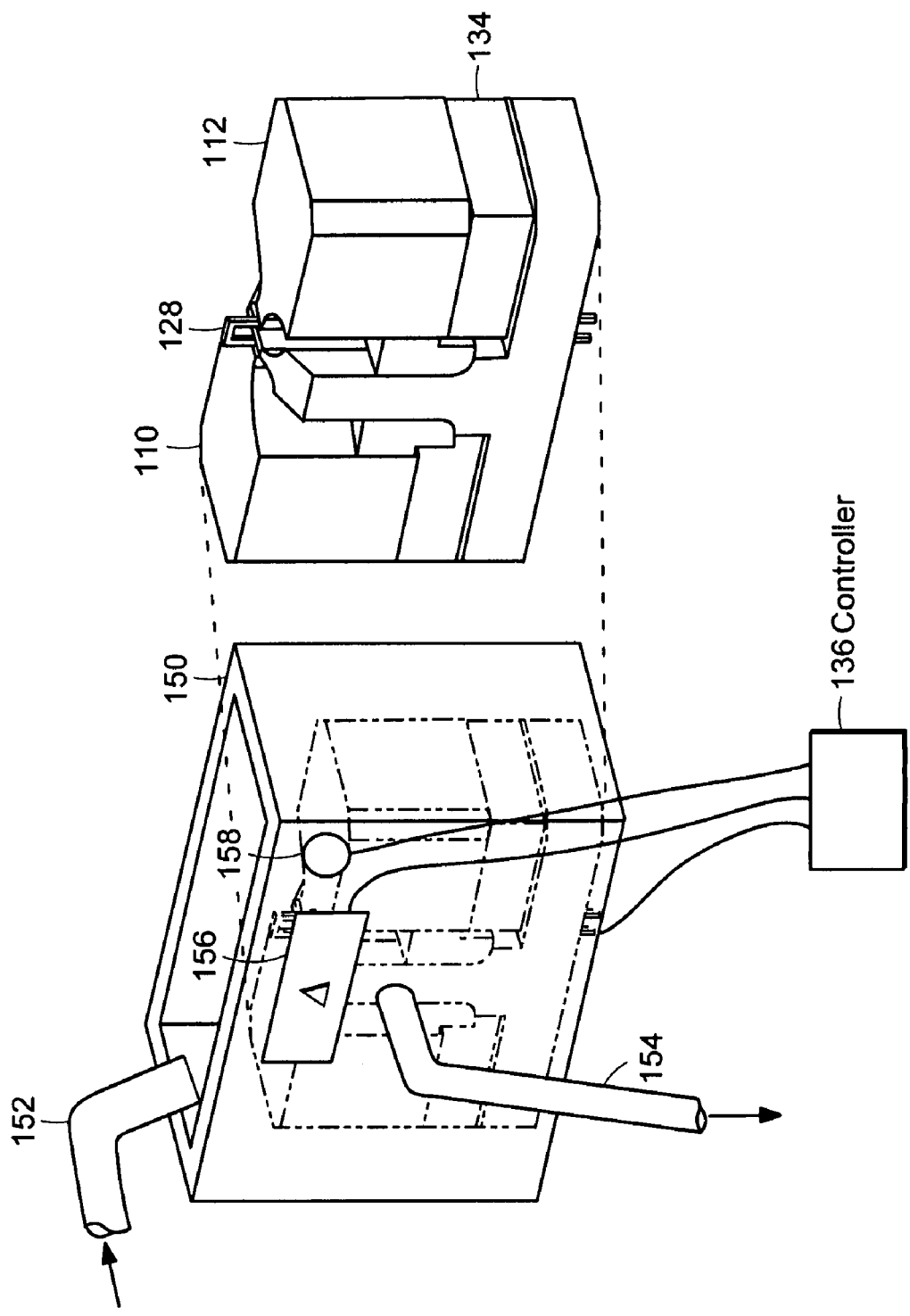
FIG. 4 depicts further embodiments relating to the sample zone such as sample chamber 150.

FIG. 4 depicts further embodiments relating to the sample zone. An sample chamber 150 can be located at the apparatus, and can encircle at least a portion of the apparatus, e.g. cantilever 128 (workpiece/cantilever 130 is not shown for clarity). Sample chamber 150 can support a liquid sample at the sample zone. For example, when the sample includes a biological tissue, e.g. a muscle cell such as a cardiac myocyte, the liquid can be a biocompatible liquid such as water, saline solution, plasma, blood, a nutrient broth, intracellular fluids, solutions of pharmaceuticals, combinations thereof, and the like. Sample chamber 150 can include inlets/outlets 152/154, which can be employed to recirculate the liquid or flow the liquid over the sample. Another optional component is a heat exchanger 156 thermally coupled to the sample zone, e.g., a thermoelectric element, a resistive heater, a heat sink, a recirculated fluid heat exchanger, and the like, which can be coupled to controller 136 to automatically raise or lower the temperature at the sample zone, maintain a desired temperature, and the like. An optional thermal sensor 158 can also be employed. The temperature can be controlled to condition a sample, for example, to maintain the viability of living cells, or to examine the function of cells versus temperature. Additionally, mechanical characterizations can be conducted as a function of temperature.

For example, in various embodiments, the biocompatible fluid can be temperature controlled by the heat exchanger to within about 0.05° C. over the range 5°-40° using a linear temperature sensing element and thermoelectric cooler on the underside of the fluid bath. The control can be implemented using delta modulation, a special case of differential pulse code modulation (DPCM). In some cases this control could be implemented using the digital circuit elements described above.

The methods and apparatus described above can be employed in various embodiments to control one or more of the following experimental variables, for example, force (stress) and displacement (strain) applied to a sample, the temperature of the sample, the composition of the fluid surrounding the sample; an electric field established across the sample using electrodes; patch clamping (e.g., to perform electrophysiological measurements on small regions of a cell membrane, such as on ion channels in the cell membrane); and the like. Testing strategies can be developed by varying one or more of these variables while holding the remaining variables constant.

For example, mechanical tests can observe the static and dynamic relationship between stress and strain, in some embodiments measuring these values as a function of: temperature (temperature sweep); biocompatible fluid composition (a sweep of the concentration of a component of the solution); and the like. For example, when the sample is a muscle these mechanical tests can be employed while the muscle is contracting, while the muscle is patch clamped after the muscle has been stimulated with an electric field; and the like.

Another example of a mechanical test is dynamic stiffness, where a linear model of a mechanical system can be described as a complex number representing the ratio of stress to strain at different frequencies. Alternatively, it can be described as the transfer function between and applied strain and the resulting stress. Methods for characterizing dynamic stiffness include swept sine system identification and stochastic system identification. Both methods apply a dynamic signal as a stress and measure the resulting strain or vice versa, however typically when computing dynamic stiffness using the data, stress is always the output and strain the input. In swept sine system identification, sinusoidal strains/stresses of different frequencies can be applied and the amplitude and phase of the resulting stress/strain can be measured. In stochastic system identification a stochastic process that excites all frequencies within the desired measurement bandwidth can be applied and a least squares estimate of the mechanical impulse response can be found using a matrix equation based on estimates of the auto and cross correlation functions.

Another example of a mechanical test is creep recovery, where a static stress can be instantaneously applied and the change in strain can be measured over time (the creep period). The stress can then be removed and the strain can be measured over a further period (the recovery period). If the sample has a linear relationship between stress and strain then its mechanical response to the creep recovery test could be predicted using the dynamic stiffness.

An example of another technique that can be combined with mechanical testing is the patch clamp, which can used to measure a broad collection of electrophysiological parameters including the intracellular potential, the amount of current flowing across the membrane, identification of ions and channels responsible for current and potential, and the like. The patch clamp technique could also be used to apply a given intracellular potential. Furthermore, in embodiments where two cantilevers are employed in conjunction with a closed feedback loop, a point on a cell sample can be held stationary with respect to the patch clamp while applying mechanical stimuli allowing concurrent or near concurrent measurement of electrophysiological parameters along with the mechanical and muscle physiology tests described herein. Also, in some embodiments, patch clamp measurements can be recorded versus temperature, versus composition of the biocompatible solution, and the like.

In embodiments where the sample is a muscle cell, common physiological tests can be conducted. For example, the muscle cell can be stimulated either electrically or chemically and can be allowed to shorten a predetermined amount before being rapidly stretched back to its original length. The time course of the force redevelopment can be measured and fit to an exponential estimate the time constant (or rate) of tension redevelopment.

In another example, the relationship between the peak or steady state force produced by a muscle and the concentration of calcium in the surrounding solution can be measured by bathing the cell in a solution with a given concentration of Ca2+ and measuring the time course of the force. The peak and steady state values can be recorded, after which the cell can be washed with a relaxing solution with relatively low Ca2+ before the experiment is repeated at a new Ca2+ level.

In still another example, the muscle cell can be stimulated either electrically or chemically, the stimulus can be removed and the force produced by the cell can be recorded over time. The decay in force can be fit to an exponential giving an estimate of the time constant of relaxation.

A particular embodiment of a mechanical characterization apparatus includes a center magnetic pole is aligned between two outer magnetic poles. Two conductive cantilevers, have at the supported end of each two legs electrically isolated from the poles, wherein the legs are supported opposite each other across the center pole and between the outer poles. A sample zone is defined by opposing faces of the cantilevers. At least one displacement sensor directed to the conductive cantilevers. A controller is included that is electrically coupled to the legs of each cantilever to independently apply current to each cantilever and correlate the current with the force at each cantilever. The controller is coupled to the displacement sensor to independently correlate the displacement of each cantilever with the force at each cantilever. The controller includes a feedback control loop that dynamically controls the displacement of a sample in the sample zone.

A particular embodiment of a method of mechanically characterizing a sample, includes a step of directing a magnetic field through two supported legs of each of two conductive cantilevers, the field direction in one leg of each cantilever being opposite the direction in the other leg of that cantilever. Also included is a step of automatically actuating each conductive cantilever independently by applying current through the legs, wherein a force created in the two legs of each cantilever is in the same direction. Another step is mechanically characterizing a sample by correlating the current with the force between each cantilever and the sample, wherein the sample is located in a sample zone defined by parallel opposing faces of the free ends of the cantilevers. Yet another step is automatically detecting the displacement of each cantilever independently, and correlating the displacements with the forces. Still another step is automatically controlling the displacement of the sample in the sample zone by operating a feedback control loop between the displacements and the current applied to the cantilevers.

The methods and apparatus disclosed herein provide significant advantages for mechanically characterizing samples, in particular biological cells such as single myocytes. Compared to existing systems, the apparatus and methods disclosed herein can be compact, modular, and low cost, while providing position resolution of about 1 nanometer/$\sqrt{Hz}$ force resolution about 10 nanoNewtons/$\sqrt{Hz}$ or less over a bandwidth of up to about 1000 Hz. A further advantage is that various embodiments disclosed herein allow both ends of a cell to be actuated, unlike commercial devices typically used for mechanically characterizing cardiac myocytes. This allows the mechanical properties of a cell to be measured while making a point on the cell surface stationary with respect to a sample analyzer such as an optical detector or a patch clamp electrophysiology sensor. Further, the design is flexible and robust, and can be easily scaled to accommodate larger forces and displacements by adjusting the dimensions of the cantilever and the current source. Another advantage is that a feedback loop can be employed to artificially increase the stiffness of the force sensing cantilever without sacrificing resolution by controlling its displacement. Also, the ability to characterize single myocytes can help to avoid complications seen in multicellular preparations, for example heterogeneity of cell types, diffusion limited transport in extracellular spaces, non-uniform shortening of sarcomeres during isometric contraction and the mechanical influence of the extracellular matrix. Finally, the low cost, modular, compact nature of the apparatus is well-suited for use in a high-throughput array.

EXEMPLIFICATION

The cardiac myocyte can be a key experimental system for exploring the contractile properties of the diseased and healthy heart. Myocytes can avoid problems inherent to multicellular preparations including heterogeneity of cell types, diffusion limited extracellular spaces, non-uniform shortening of sarcomeres during isometric contraction, and the mechanical influence of the extracellular matrix, and can allow clear optical interrogation of sarcomere length. Furthermore, the contractile apparatus in a single cell can be arrayed in a physiologically relevant orientation (an advantage over single molecule or single myofibril studies).

Example 1 describes development of a modular instrument that has performed dynamic stiffness measurements on a test fiber. The mechanical and electrical characteristics of the device are presented and its functionality demonstrated by actual measurement results of dynamic stiffness of a compliant polymer fiber. Example 2 describes guidelines believed to be appropriate for applying the methods and apparatus disclosed herein in combination with the results of Example 1 to experiments on actual muscle cells.

Mechanical Application Example 1

The particular implementation in this example includes two stainless steel cantilevers (cut from 25 μm foil using a Charmilles Robofil 1020SI wire electrical discharge machine (EDM)) with a rectangular section removed from the center. These cantilievers function as Lorentz force actuators that can simultaneously be used as force sensors. Vanadium Permandur keepers (magnetic poles) guide the magnetic field and concentrate it between the poles in two air gaps. The core of the motor structure is coated in 2 μm of parylene (applied with a Para Tech 3000 Lab Top deposition system) to provide biologically compatibility. Confocal optical displacement sensors reflect from the back surface of each cantilever and the resulting photodiode current can be amplified and can then be used as a control input to a current source controller driving the actuator.

All electronics except those for data acquisition are built into the module in this example. For example, in various embodiments, an analog circuitry can be employed to amplify the position signal and to drive current through the cantilever. Design principles for such a circuit are illustrated in Brenan C, Doukoglou T, Hunter I, Lafontaine S. Characterization and use of a novel optical position sensor for microposition control of a linear motor. Rev Sci Instrum. 1993 February; 64(2): 349-356; and Horowitz P, Hill W. The art of electronics 2nd Ed. Cambridge University Press. 1997; the entire teachings of these documents are incorporated herein by reference.

Data Acquisition, Control and Signal Processing

Currently, data acquisition and real time digital control are implemented using a commercial data acquisition card (a 6052E National Instruments (NI-DAQ), National Instruments, Austin Tex.) and custom code. Four analog inputs are each sampled at 20 kHz (two position signals and two current signals) and two analog outputs set the current through the cantilevers. Signal processing algorithms have been implemented in that can perform swept sine and stochastic system identification and extract mechanical Markov parameters.

A typical experiment to probe the impulse response of a cantilever applied a 2×10$^5$ point current (force) signal produced by shaping and scaling zero mean, unit variance, approximately Gaussian white noise. The peak displacement and force were <20 μm and <160 μN respectively. The resulting displacement was measured and 2048 point auto and crosscorrelation estimates were made using force and position data. Levinson recursion was implemented to invert the Toeplitz matrix of autocorrelation coefficients and produce a 2048 point estimate of the Markov parameters. The quality of the system identification was assessed by calculating the variance accounted for or coherence squared (coh$^2$) according to $$coh^2 = \frac{|S_{xy}(j\omega)|^2}{|S_{xx}(j\omega)||S_{yy}(j\omega)|} \qquad (2)$$

where $S_{xy}(j\omega)$, $S_{xx}(j\omega)$ and $S_{yy}(j\omega)$ are the Fourier transforms of the cross and autocorrelations of the input (x) and output (y). A coh$^2$ below one indicates the presence of noise in the data or nonlinearities in the system under test.

Figure 5:
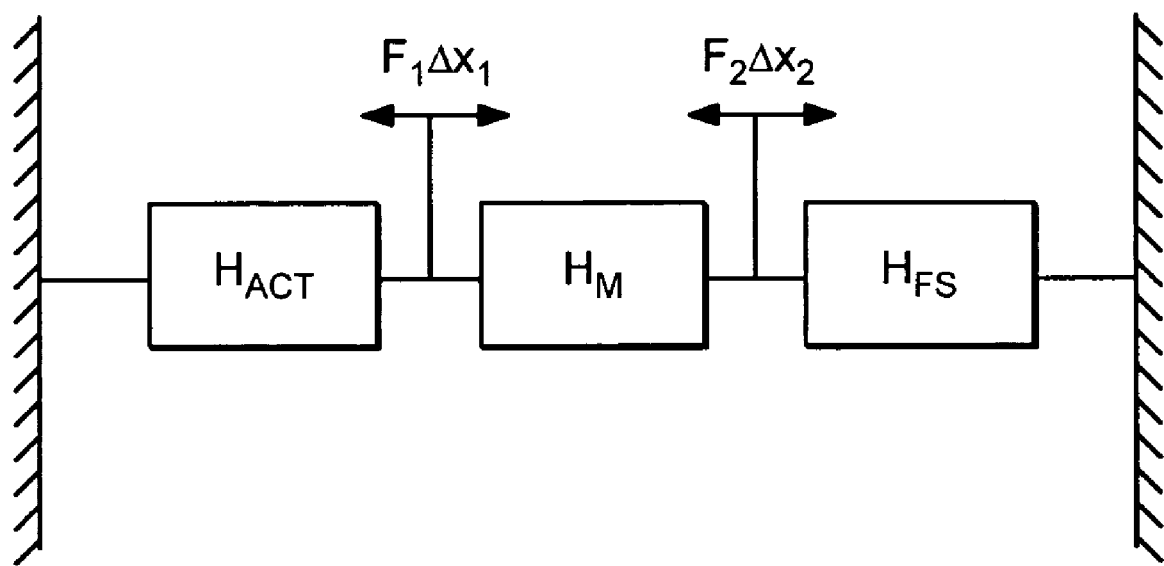
FIG. 5 schematically depicts the lumped parameter system model. $H_M(j\omega)$, $H_{ACT}(j\omega)$, $H_{FS}(j\omega)$ are the dynamic stiffness of the sample, actuator and force sensor respectively. Forces and displacements can be applied on either side of the sample

To explore the properties of a sample suspended between the cantilevers, a current was applied to one cantilever (the actuator) and its displacement and that of the other cantilever (the force sensor) were measured. A finite element model was used to explore the loading effects of a sample (with material properties similar to a myocyte) on the dynamics of the system using harmonic analysis (ANSYS, ANSYS Inc., Canonsburg, Pa.). It was found that at frequencies below resonance, lumped parameter models of the two cantilevers were adequate to estimate the dynamics of the material under test using $$H_M(j\omega) = \frac{1}{\frac{1}{H_{OBS}(j\omega) - H_{ACT}(j\omega)} - \frac{1}{H_{FS}(j\omega)}} \qquad (3)$$

where $H_M(j\omega)$, $H_{ACT}(j\omega)$, $H_{FS}(j\omega)$ and $H_{OBS}(j\omega)$ are the dynamic stiffness of the material, the actuator cantilever, the force sensor cantilever and the loaded actuator (observed response of the actuator when loaded). In calculating $H_M(j\omega)$, 2$^{nd}$ order models fit to previously measured cantilever transfer functions were used for $H_{ACT}$ and $H_{FS}$. FIG. 5 schematically depicts the lumped parameter system model. $H_M(j\omega)$, $H_{ACT}(j\omega)$, $H_{FS}(j\omega)$ are the dynamic stiffness of the sample, actuator and force sensor respectively. Forces and displacements can be applied on either side of the sample.

Position Sensing

The resolution of the displacement sensor relates to the minimum detectable force and position. A commercially available confocal sensor consisting of a LED, split lens and photodiode (HEDS-1300, Agilent, Palo Alto, Calif.) was selected for its simplicity, robustness and ease of alignment.

A transimpedance amplifier was designed such that the position resolution was limited by the shot noise of the photodiode within the HEDS-1300 device. Circuit noise and interference were quantified at several operating points (currents levels through the photodiode) using a 25 µm stainless steel foil mounted on a piezoelectric actuator (PI 841.1, Physik Instrumente, Auburn, Mass.) as a reflective surface. The power spectra of the position signal was estimated in software via periodogram averaging of 20, 524288 point signals (sampling at 60 kHz).

Figure 6A:
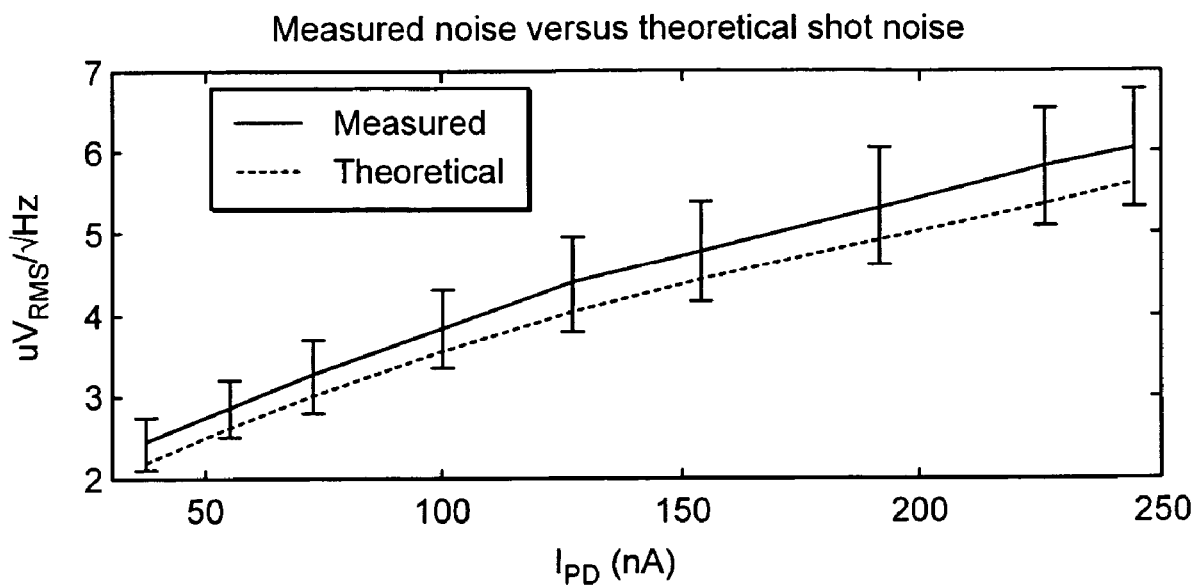
FIG. 6A depicts average measured noise on the position signal between 100 Hz and 1 kHz and theoretical shot noise versus current through the photodiode.

FIG. 6A compares average noise between 100 Hz and 1 kHz and the theoretical shot noise at the amplifier output (circuit gain $20 \times 10^6$ V/A) for different photodiode currents demonstrating that the circuit can be shot noise limited over the majority of the measurement bandwidth.

Figure 6B:
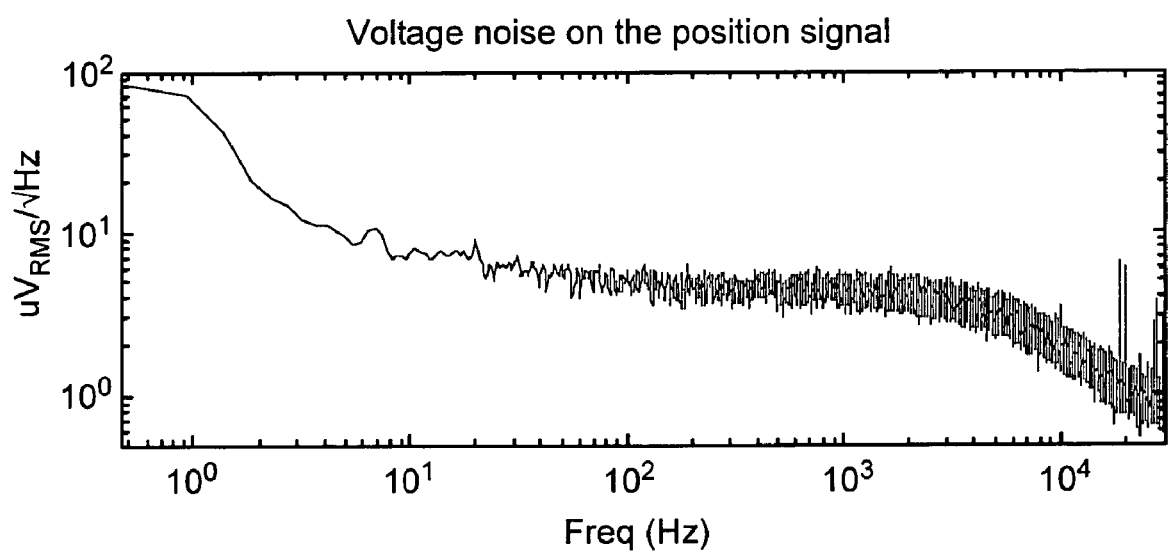
FIG. 6B depicts a typical power spectrum estimate. The average noise between 100 Hz and 1 kHz is approximately 4.6±0.5 $\mu V/\sqrt{Hz}$. The theoretical shot noise is 4.83 $\mu V/\sqrt{Hz}$.

A characteristic power spectral density is presented in FIG. 6B. In this case, the average noise was approximately $4.6 \pm 0.5$ µV/$\sqrt{Hz}$ compared to the theoretical shot noise of 4.83 µV/$\sqrt{Hz}$ (183 nA photodiode current). This is equivalent to 0.22 nm/$\sqrt{Hz}$ position noise given that the sensitivity of the detector was 21.2 kV/m at this operating point (calibrated using the piezoelectric actuator).

System Calibration

Each position sensor was calibrated in the apparatus using a digital microscope focused on the top edge of the cantilever as it was being driven by a 1 Hz sinusoidal current. Custom edge detection code (written in Matlab, MathWorks, Natick, Mass.) was used to track the displacement and the sensitivity of the digital microscope was calibrated to 4.6 pixels/µm using a 10 µm graticule.

The relationship between force and current was calibrated using a strain gauge (FORT 10, World Precision Instruments, Sarasota Fla.) mounted on the piezoelectric actuator. The strain gauge was pushed against the cantilever, zeroed and then sinusoidal currents were applied to the cantilever. Sinusoids were fit to the force and current data using non-linear least squares estimation (LSE). The sensitivities of each cantilever were approximately the same and were typically between $1.1 \times 10^{-3}$ and $1.3 \times 10^{-3}$ N/A corresponding to an air gap magnetic flux density of approximately 1 T. To measure the stiffness of each cantilever (typically between 6 to 8 N/m at 0 Hz) the force sensor was pushed against the cantilever, zeroed and then sinusoidal displacements were applied using the piezoelectric actuator.

A finite element model of the cantilever structure was generated using ANSYS. Eleven simulations were run over a range of lengths from 3 to 4 mm. The change in the first resonant frequency and the stiffness at 0 Hz (estimated by applying a 1 milliNewton force distributed across the top edge) were recorded and could be fit to $2^{nd}$ order polynomial functions of cantilever length.

Figure 7:
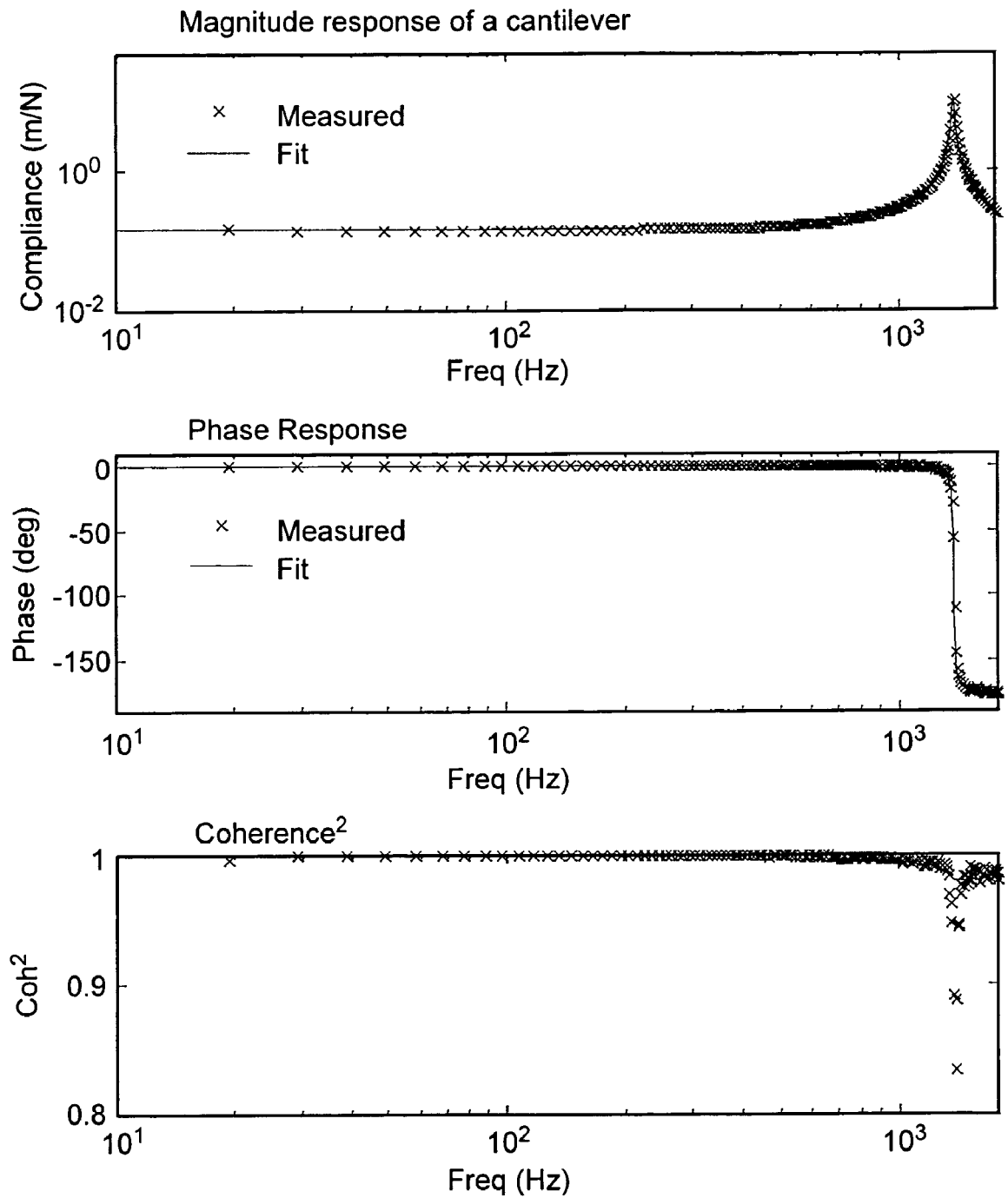
FIG. 7 depicts the mechanical transfer function of one of the cantilevers and the $coh^2$ of the system identification. The $2^{nd}$ order impulse response fit to the data had parameters k=6.84 N/m, $\omega_n$=1.39 kHz and $\zeta$=0.006425. The FEM predicted a stiffness of 6.83 N/m for this $\omega_n$.

FIG. 7 depicts the mechanical transfer function of one of the cantilevers and the $coh^2$ of the system identification. The $2^{nd}$ order impulse response fit to the data had parameters k=6.84 N/m, $\omega_n$=1.39 kHz and $\zeta$=0.006425. The FEM predicted a stiffness of 6.83 N/m for this $\omega_n$. The calibration results were used in conjunction with stochastic system identification to measure the mechanical transfer function of each cantilever between 0 Hz and 10 kHz. The measured Markov parameters were fit to a $2^{nd}$ order mechanical impulse response using nonlinear LSE. The resonant frequency and the FEM results provided a means of confirming the stiffness of the cantilevers and hence validating the calibration of the position and force sensors.

Mechanical Application Example 1

Results

The dynamic stiffness of a 5 µm diameter, 85 µm long polymer fiber (a composite of thermoplastic polyurethane and hydrocarbon) was measured between 0 Hz and 500 Hz using stochastic system identification. The fiber was mounted by draping it over the center of the cantilevers and then lightly pressing on it. Subsequent inspection of the bond under a digital microscope revealed no slipping even when displacements as large as 50 µm were applied.

Figure 8:
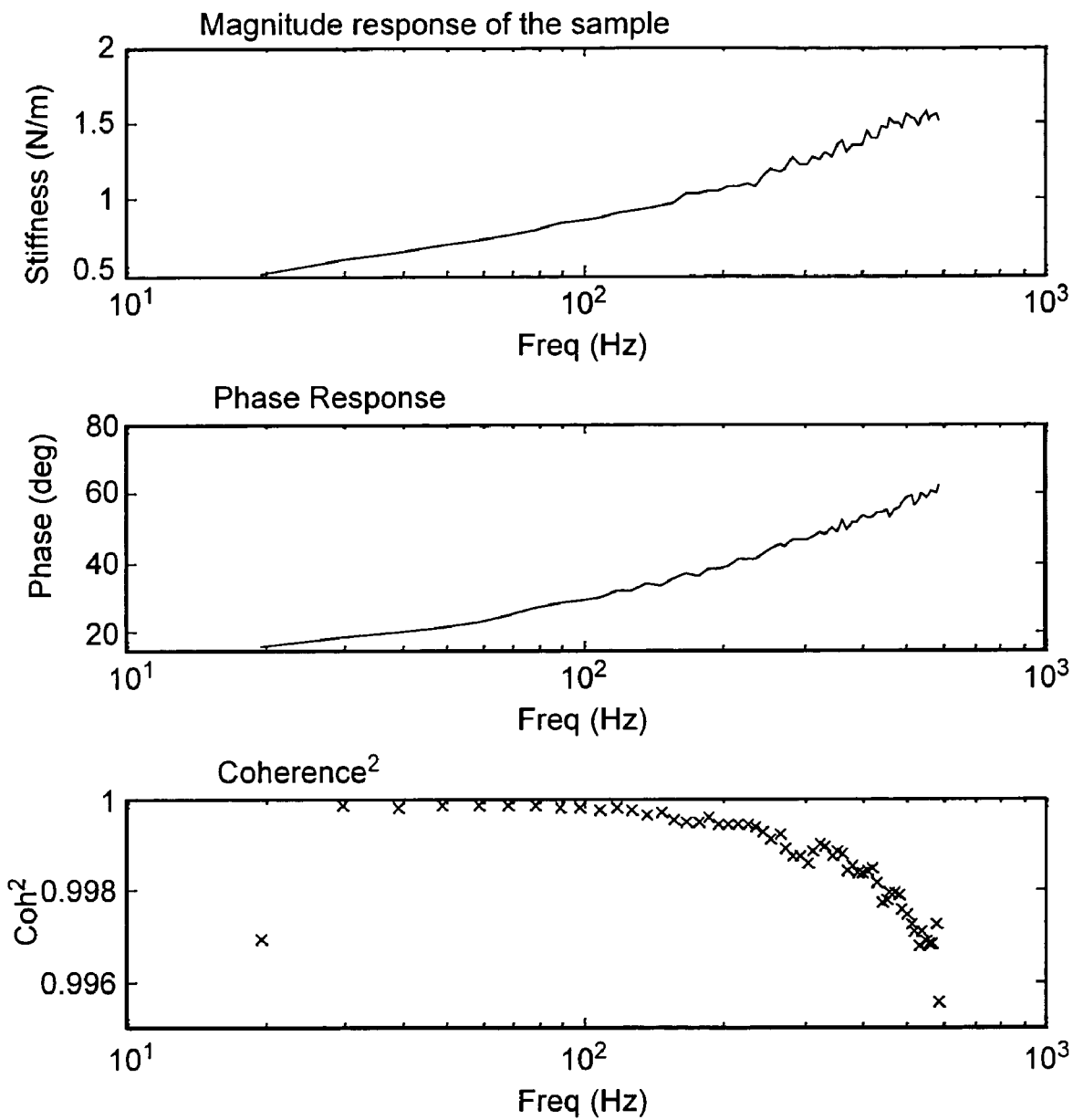
FIG. 8 depicts the dynamic stiffness of a 5 μm diameter, 85 μm long polymer fiber and the $coh^2$ of the measurement. The DC stiffness is of the same order of magnitude as that of a myocyte.

A $2 \times 10^5$ point, white, Gaussian force sequence was band limited using a $1^{st}$ order filter with a 100 Hz 3 dB point and applied to one cantilever (the actuator). The resulting 0 mean, $1.68 \times 10^{-11}$ m$^2$ variance Gaussian displacement of the actuator was recorded as was the motion of the other cantilever (the force sensor). The Markov parameters relating the position of the actuator to the position of the force sensor were calculated using system identification techniques. The impulse response of the sample was estimated using (3). FIG. 8 presents the results, depicting the dynamic stiffness of a 5 µm diameter, 85 µm long polymer fiber and the $coh^2$ of the measurement. The DC stiffness is of the same order of magnitude as that of a myocyte.

The stiffness of the fiber at 0 Hz was approximately 0.3 N/m and its Young's modulus was 0.3 MPa (assuming uniform cross section)

Discussion

Currently, low frequency measurements appear to be affected by drift in the position signal (see FIG. 12B) which is believed to be thermal in origin. This can be addressed in the future iterations by monitoring the temperature of the sensor and correcting for relative temperature change. The slight drop in the $coh^2$ at low frequencies in FIG. 13 can result from this drift while the drop in $coh^2$ at resonance can be due to mild clipping of the position signal.

The low frequency drift also appears to be evident in the $coh^2$ presented in FIG. 14. Furthermore, the current signal applied to the actuator in this case was band limited to 100 Hz, which appeared to roll off in $coh^2$ above this frequency due to decreasing signal to noise ratio. In the future it can be desirable to apply displacement sequences with a standard deviation of 100 nm (approximately 4 µm was used in this study) which can employ careful alignment of the position sensors and application of system identification methods to address the decrease in signal to noise ratio.

Application Example 2

Characterization of Myocytes

The following section provides guidelines and expectations believed to be appropriate for characterizing myocytes by employing the disclosed apparatus and methods.

Guidelines for Isometric measurements

Murine myocytes are approximately 110 µm long, $300 \times 10^{-12}$ m$^2$ in cross section, have sarcomere lengths between 1.7 and 2.3 µm and produce approximately 10 µN of peak force. To perform isometric measurements it is desirable for the stiffness of the force transducer to be >100 N/m (≈0.1% transducer strain under peak force). The full physiological range of muscle length corresponds to ≈30% strain and spans the nonlinear ascending limb of the classic force length relationship from resting to peak force. Thus, 0.1% strain corresponds to approximately 0.3% of physiological range and would result in a tolerable change in force of ≈0.3% (30 nN). In addition, for a cantilever based force transducer this requires the minimum resolvable position to be considerably below 100 nm.

Myocyte Stimulation

There are two common preparations of myocytes for exploring the mechanics of cardiac myocytes, skinned cells in which the membrane has been permeabalized (first introduced by Natori in 1954) and intact cells. The former allow more precise control of the environment surrounding the muscle fibres and the exchange or partial replacement of some regulatory proteins. The latter cells are technically alive, maintain physiological separation of actin and myosin and suffer less from disruption of signaling pathways. We propose to incorporate the ability to experiment on both preparation types however the stimulation of contraction is different in each type.

Skinned cells can be stimulated by rapidly changing the solution in the myocyte bath from relaxing, $[Ca^{2+}]<10\,\mu M$, to contracting, $[Ca^{2+}]<100\,\mu M$. Appropriate solutions can be selected from the literature, see, for example, (Weiward, W. K., et al., *J. Mol Cell Cardiol* 2000 February: 32(2): 247-59; and Swartz, D. R., et al., *J Physiol.* 2001 Jun. 1: 533(Pt 2): 357-65). Free ionic concentrations can be predicted according to Fabiato (Fabiato, A., *Methods Enzymol.* 1988. 157: 378-417). The timescale for diffusion into the cell with radius 20 µm at 20° C. is approximately 400 ms (assuming $D_{ion} \approx 10^{-9}\,m^2/s$) and can be inversely proportional to temperature (Deen, W. M., *Analysis of Transport Phenomena.* Oxford University Press, 1998). A bath change cycle time of 20 ms can allow for multiple washes within 100 ms. Given the bath volume can be constructed to be less than 100 µL, the required flow rate of 5 mL/s can be achievable.

An electric field is required to stimulate twitches in intact cells. Platinum electrodes can be inserted parallel to the long axis of a myocyte and step changes in electric field of up to 500 V/m applied at frequencies between 0.1 and 10 Hz similar to Cheng, et al. (Cheng, D. K., et al., *Am J Physiol.* 1999 July: 277(1 Pt 2): H351-62; and Stuyvers, B. D., et al., *J Physiol.* 2002 Nov. 1; 544 (Pt 3): 817-30). Potential for unwanted current flow between the electrodes due to faradic or non-faradic processes will be explored theoretically and experimentally. The link between EC coupling and cross bridge cycle kinetics can be explored directly through parallel measurement of the stress-stimulation frequency response of muscle between 0.1 and 10 Hz and mechanical transfer function at greater frequencies.

Guidelines for Sarcomere Length Detection

A laser diffraction system can be employed to measure sarcomere length based on the approach of Stuyvers, et al. (Stuyvers, B. D., et al., *J Physiol.* 2002 Nov. 1; 544 (Pt 3): 817-30; and Stuyvers, B. D., et al., *J Physiol.* 1997 Aug. 1; 502 (Pt 3): 661-77). Briefly, the beam of laser diode may be projected onto the muscle from the side of the device. A collimating lens and possibly a focusing lens may be required to limit the divergence and spot size of the beam. The $0^{th}$ and $1^{st}$ order peaks of the diffraction pattern produced by individual myocytes are often well separated however if necessary the technique described by Van Heuningen, et al. (Van Heuningen, R., et al., *Am J Physiol.* 1982 March: 242(3): H411-20). can be used compensate for interference between the orders. The two first order bands may be detected separately using a photodiode array and a lateral effect photodiode and the sensitivity of each will be calibrated using an optical grating. Once calibrated, the combination of two detectors will allow the laser to be aligned directly with the quasi-crystalline structure of the myocyte (when the signals from both are equal). This limits the so called Bragg angle effect (Syuyvers, B. D., et al., *J Physiol.* 1997 Aug. 1; 502 (Pt 3): 661-77; and Goldman, Y. E., *Biophys J.* 1987 July; 52(1): 57-68). Automation of the process in a final device in which the position and angle of the myocyte vary between experiments will present a challenge possibly requiring actuation of the beam path.

Exploring Regulation of Contraction—Dynamic Characterization Guidelines

Dynamic mechanical properties of muscle have been probed at the cellular level using step, ramp and sinusoidal changes in length and concentrations of externally accessible reactants in the cross bridge cycle (see review (Cabridge Technology. Http://www.camtech.com. May 2003.)). If the muscle is assumed to be linear then, under the same experimental conditions, measurement of the stiffness frequency response should return similar information to the above perturbations. Although the mechanical transfer function of muscle tissue is being increasingly used in the exploration of the contraction (Wang, G., et al., *J Physiol.* 2001 Feb. 15; 531 (Pt 1):219-34; Kawai, M., et al., *Circ Res.* 1993 July; 73(1): 35-50; Landesberg, A., et al., *Am J Physiol.* 1994 August; 267 (2 Pt 2): H779-95; Regnier, M., et al., *Am J Physiol.* 1995 December; 269 (6 Pt 1): C1532-9; and Campbell, K. B., et al., *Biophys J.* 2001 October; 81(4): 2278-96), to date it has only been measured in trabeculae as swept sin analysis of muscle tissue requires <0.1% strain to ensure the response remains linear (Kawai, M., et al., *J Muscle Res Cell Motil.* 1980 September; 1(3): 279-303) corresponding to a 100 nm displacement for a myocyte. Measured spectra are often fit to a transfer function containing three or four exponential processes and the rates of these related to the cross bridge cycle (Kawai, M., et al., *J Muscle Res Cell Motil.* 1980 September; 1(3): 279-303). More elaborate experiments have attempted to deduce complete crossbridge cycle models from stiffness spectra (up to 19 parameters (Campbell, K. B., et al., *Biophys J.* 2001 October; 81(4): 2278-96)). Another limitation of current measurements of the mechanical transfer function is the dynamic range bandwidth product of the experimental instrument. It has been suggested that swept sign analysis of muscle band limited to <250 Hz was unable to capture high frequency features (Wang, G., et al., *J Physiol.* 2001 Feb. 15; 531(Pt 1): 219-34) implying the use of a larger bandwidth for system identification will return more information.

Excitation-Contraction (EC) Coupling Guidelines

Further information can be gleaned from intact myocytes by considering the transfer function between applied electric field frequency and the resulting peak stress (typically referred to as the stress-frequency relationship SFR). An electric field is required to stimulate twitches in intact cells via net depolarization of the membrane, influx of $Ca^{2+}$ through L-type channels, release of $Ca^{2+}$ from the sarcoplasmic reticulum and contraction via the EC coupling mechanism (see review (Noble, D., et al., *Phil trans R Soc Lond A.* 2001; 359: 1127-1142)). SFR measurements are typically performed in murine models at frequencies between 0.1 Hz and 8 to 12 Hz (corresponding to the peak physiological heart rate of 500 and 700 beats/min in mice) (Stuyvers, B. D., et al., *J Physiol.* 2002 Nov. 1; 544(Pt 3): 817-30). Above these frequencies the induced twitches begin to fuse leading to tetanus. The shape of the SFR in murine models and hence its interpretation is currently a contentious issue with researchers presenting conflicting results (see reviews (Bers, D. M., *Circ Res.* 2000 Aug. 18; 87(4): 275-81; and Bers, D. M., *Nature.* 2002 Jan. 10; 415(6868): 198-205)). Despite this, attempts have been made to link its features to the transport of ions with recent work suggesting that it is strongly dependent on the balance $Ca^{2+}$ from the sarcoplasmic reticulum and exterior of the cell. As with the mechanical transfer function, the SFR has only been measured in trabeculae that suffer from metabolic failure at high frequencies due to insufficient $O_2$ (Stuyvers, B. D., et al., *J Physiol.* 2002 Nov. 1; 544(Pt 3): 817-30). The SFR can be measured in myocytes and further to simultaneously measure the higher frequency region of the mechanical transfer function where both excitation contraction coupling and the kinetics of the cross bridge cycle can be explored in parallel.

The entire teachings of each cited reference is incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. An electromagnetic apparatus, comprising:
   a conductive loop comprising two parallel conductive legs joined at a free end by a sample contacting member sized to act upon a small sample; and
   a magnetic circuit that imposes a magnetic field, the magnetic field having magnetic vectors in opposite directions across the respective legs;
   an electric current flowing in opposite directions through the conductive legs, the interaction between the magnetic vectors and the electric current causing an imposed force on the parallel legs; and
   a sensor for sensing a response of the sample.

2. The apparatus of claim 1, wherein the electric current flowing in opposite directions through the conductive legs results in movement of the member in a direction normal to its surface.

3. The apparatus of claim 2, wherein the magnetic circuit comprises a center magnetic pole aligned between two outer magnetic poles, the conductive loop electrically isolated from the poles, and the legs supported opposite each other across the center pole and between the outer poles; and
   a workpiece opposing the sample contacting member to define a sample zone, the sample zone being between the face of the workpiece and the sample contacting member.

4. The apparatus of claim 3, wherein the loop is a conductive cantilever comprising the two legs at its supported end.

5. The apparatus of claim 4, further comprising a displacement sensor directed at the conductive cantilever.

6. The apparatus of claim 4, wherein the workpiece is the free end of a second conductive cantilever.

7. The apparatus of claim 3, wherein the workpiece is an anvil.

8. The apparatus of claim 5, further comprising a controller electrically coupled to the legs of the cantilever, the controller actuating the cantilever by applying current and correlating the current with the force at the cantilever.

9. The apparatus of claim 8, wherein the controller is coupled to the displacement sensor, the controller correlating force with displacement upon actuation of the cantilever.

10. The apparatus of claim 9, wherein the workpiece is the free end of a second conductive cantilever, the controller being electrically coupled to the legs of each cantilever, and the controller independently actuating each cantilever by applying current and correlating the current with the force at each cantilever.

11. The apparatus of claim 10, wherein the displacement sensor is directed at both conductive cantilevers, the controller independently detecting force as a function of displacement upon actuation of each cantilever.

12. The apparatus of claim 10, further comprising a second displacement sensor directed to the second conductive cantilever and coupled to the controller, the controller independently detecting force as a function of displacement upon actuation of each cantilever.

13. The apparatus of claim 10, wherein the controller comprises a feedback control loop that dynamically controls the displacement of a sample in the sample zone.

14. The apparatus of claim 8, wherein the controller dynamically detects force and displacement of the cantilever over a bandwidth of at least 250 Hz.

15. The apparatus of claim 14, wherein the controller dynamically detects force and displacement of the cantilever from 0 Hz to 500 Hz.

16. The apparatus of claim 15, wherein the controller dynamically detects force and displacement of the cantilever from 0 Hz to 1000 Hz.

17. The apparatus of claim 14, wherein the controller dynamically detects force of the cantilever at a resolution of 100 nanoNewtons/Hz.

18. The apparatus of claim 14, wherein the controller dynamically detects displacement of the cantilever at a resolution of 10 nanometers/Hz.

19. The apparatus of claim 3, wherein the sample zone is from 1 micrometer to 1000 micrometers across.

20. The apparatus of claim 3, further comprising a biocompatible coating at the sample zone.

21. The apparatus of claim 20, wherein the biocompatible coating is selected from gold; titanium; titanium alloys; platinum; alloys of platinum, palladium, rhodium, iridium, ruthenium, and osmium; parylene; polymethyl methacrylate; polyethylene terephthalate; polypropylene; polytetrafluoroethylene; ultrahigh molecular weight polyethylene; polyethylene oxide; and polyvinyl pyrrolidone.

22. The apparatus of claim 20, further comprising a sample chamber that encircles at least a portion of the conductive cantilever and the workpiece to support a liquid sample in the sample zone.

23. The apparatus of claim 22, further comprising an inlet and an outlet at the sample chamber.

24. The apparatus of claim 22, further comprising a heat exchanger thermally coupled to the sample zone.

25. The apparatus of claim 3, further comprising a plurality of electrodes, the electrodes generating an electric field at the sample zone.

26. The apparatus of claim 3, further comprising a patch clamp sensor that contacts a sample in the sample zone.

27. The apparatus of claim 3, further comprising an optical detector that observes a sample in the sample zone.

28. The apparatus of claim 3, wherein the center pole supports a magnetic polarity opposite from the outer poles.

29. The apparatus of claim 28, wherein the magnetic poles support a magnetic field strength between the center pole and each outer pole from about 0.1 Tesla to about 2.5 Tesla.

30. The apparatus of claim 29, wherein the magnetic poles are a permanent magnetic material selected from alinco magnets, hard ferrite magnets, samarium cobalt magnets, and neodymium iron boron magnets.

31. The apparatus of claim 23, wherein the magnetic poles are a magnetic permeable material selected from amorphous alloys; nano-crystalline alloys; soft ferrites; MnZn ferrite; microwave ferrites; and vanadium Permandur.

32. The apparatus of claim 31, wherein the magnetic poles are coupled to an electromagnet.

33. The apparatus of claim 31, wherein the magnetic poles are coupled to a permanent magnetic material selected from alinco magnets, hard ferrite magnets, samarium cobalt magnets, and neodymium iron boron magnets.

34. The apparatus of claim 4, wherein the conductive cantilever has a stiffness (at 0 Hz) from about 0.1 to 50 Newtons/meter.

35. The apparatus of claim 34, wherein the conductive cantilever has a first resonant frequency in air of between 100 Hz to about 50,000 Hz.

36. The apparatus of claim 35, wherein the conductive cantilever is made from a material selected from a metal and a doped semiconductor.

37. The apparatus of claim 36, wherein the conductive cantilever is made from a metal selected from gold, platinum, copper, titanium, aluminum, steel alloys; nickel alloys; copper alloys; aluminum alloys; cobalt-chromium alloys; titanium alloys; and stainless steel 304.

38. The apparatus of claim 36, wherein the conductive cantilever is made from a doped semiconductor selected from doped silicon; silicon dioxide; silicon nitrite, CdTe, CdSe, CdS, ZnS, GaAs, GaN, AlGaN, InGaN, GaP, InP, InAsP, Si, Ge, ZnO, SnO2, TiO2, Cr2-xTixO3, WO3, SiC, Fe2O3, In2O3, Ga2O3, SrTiO3, BaTiO3, CaTiO3, (La,Sr)FeO3, (La,Sr)CoO3, and indium tin oxide.

39. An electromagnetic apparatus, comprising:
   first and second magnetic poles; and
   a conductive loop comprising two legs electrically isolated from the poles, the legs supported between the first and second magnetic poles, the magnetic poles directing magnetic vectors of a magnetic field in opposite directions across each leg, the conductive loop acting upon a small sample;
   an electric current flowing in opposite directions through the two legs, the interaction between the magnetic vectors and the electric current causing an imposed force on the two legs; and
   a sensor for sensing a response of the sample.

40. The apparatus of claim 39 wherein the first and second magnetic poles are of opposite polarity, the legs are supported across the first pole, and the legs and the first pole extend into a cavity defined by the second pole.

41. The apparatus of claim 39 wherein the first and second poles are of the same polarity and oppose each other to define a gap.

42. The apparatus of claim 39, further comprising a third magnetic pole aligned between the first and second magnetic poles, the first and second magnetic poles each being at an opposite magnetic polarity compared to the third magnetic pole, and the legs of the conductive loop being separated across the third magnetic pole.

43. The apparatus of claim 39, wherein the loop is a conductive cantilever comprising the two legs at its supported end.

44. The apparatus of claim 43, further comprising an anvil opposing a face of the free end of the cantilever to define a sample zone.

45. The apparatus of claim 44, further comprising a second conductive cantilever, wherein a face of the free end of each cantilever opposes that of the other cantilever to define a sample zone, the sample zone being between the faces of both cantilevers in the sample zone.

46. A mechanical characterization apparatus, comprising:
   a center magnetic pole aligned with two outer magnetic poles;
   two conductive cantilevers comprising at a supported end of each cantilever, two legs electrically isolated from the poles, the legs supported opposite each other across the center pole and between the outer poles, wherein a sample zone is defined as the area between opposing faces of the cantilevers, a magnetic field produced by the center magnetic pole and outer magnetic poles having magnetic vectors in opposite directions across each leg, the sample zone adapted to receive a small sample to be analyzed;
   an electric current flowing in opposite directions through the two legs, the interaction between the magnetic vectors and the electric current causing an imposed force on the two legs; and
   at least one displacement sensor directed to the conductive cantilevers; and a controller that:
   is electrically coupled to the legs of each cantilever to independently apply the current to each cantilever and correlate the current with the force at each cantilever; and
   is coupled to the displacement sensor to independently correlate the displacement of each cantilever with the force at each cantilever; and
   comprises a feedback control loop that dynamically controls the displacement of a sample in the sample zone.

47. An apparatus for mechanical characterization of a small sample, comprising:
   means for electromagnetically actuating two conductive cantilevers, each conductive cantilever having two parallel legs in an opposing magnetic field, the magnetic field having magnetic vectors in opposite directions across each leg, the area between opposing faces of the cantilevers defining a sample zone;
   means for applying a current in opposite directions through the two legs, the interaction between the magnetic vectors and the current causing an imposed force on the legs;
   means for independently measuring force generated by each cantilever; and
   means for measuring displacement of each cantilever and correlating the displacements and the forces.

48. The device of claim 1, wherein the magnetic vectors of the magnetic field are in opposite directions along a common axis through the two legs.

49. The device of claim 39, wherein the magnetic vectors of the magnetic field are in opposite directions along a common axis through the two legs.

50. Device of claim 46, wherein the magnetic vectors of the magnetic field are in opposite directions along a common axis through the two legs.

* * * * *